(12) United States Patent
O'Hare et al.

(10) Patent No.: US 11,993,519 B2
(45) Date of Patent: May 28, 2024

(54) LAYERED DOUBLE HYDROXIDE PRECURSOR, THEIR PREPARATION PROCESS AND CATALYSTS PREPARED THEREFROM

(71) Applicants: Oxford University Innovation Limited, Botley Oxford (GB); SCG Chemicals Co., Ltd., Bangkok (TH)

(72) Inventors: Dermot O'Hare, Oxford (GB); Shik Chi Tsang, Oxford (GB); Meng-Jung Li, Oxford (GB)

(73) Assignees: Oxford University Innovation Limited, Oxford (GB); SCG Chemicals Co., Ltd., Bangkok (TH)

( * ) Notice: Subject to any disclaimer, the term of this patent is extended or adjusted under 35 U.S.C. 154(b) by 774 days.

(21) Appl. No.: 16/491,485

(22) PCT Filed: Mar. 6, 2018

(86) PCT No.: PCT/GB2018/050567
§ 371 (c)(1),
(2) Date: Sep. 5, 2019

(87) PCT Pub. No.: WO2018/162893
PCT Pub. Date: Sep. 13, 2018

(65) Prior Publication Data
US 2020/0017368 A1    Jan. 16, 2020

(30) Foreign Application Priority Data
Mar. 6, 2017 (GB) ..................... 1703558

(51) Int. Cl.
*C01G 15/00* (2006.01)
*B01J 23/825* (2006.01)
(Continued)

(52) U.S. Cl.
CPC .......... *C01G 15/006* (2013.01); *B01J 23/825* (2013.01); *C07C 29/154* (2013.01);
(Continued)

(58) Field of Classification Search
None
See application file for complete search history.

(56) References Cited

U.S. PATENT DOCUMENTS

| 7,671,124 B2 | 3/2010 | Tsujimoto et al. |
| 11,242,460 B2 | 2/2022 | O'Hare et al. |

(Continued)

FOREIGN PATENT DOCUMENTS

| CN | 1131412 A | 9/1996 |
| CN | 101503182 A | 8/2009 |

(Continued)

OTHER PUBLICATIONS

Khzouz et al., Characterization and activity test of commercial Ni/Al2O3, Cu/ZnO/Al2O3 and prepared Ni—Cu/Al2O3 catalysts for hydrogen production from methane and methanol fuels, International Journal of Hydrogen Energy, 2013, 38, 1664-1675 (Year: 2013).*

(Continued)

*Primary Examiner* — Melissa S Swain
*Assistant Examiner* — Keling Zhang
(74) *Attorney, Agent, or Firm* — Foley Hoag LLP; David P. Halstead; Alexander J. Chatterley

(57) ABSTRACT

New layered double hydroxide materials useful as intermediates in the formation of catalysts are described, as well as methods of preparing the layered double hydroxides. Also described are catalysts suitable for catalysing the hydrogenation of $CO_2$ to methanol, as well as methods for preparing the catalysts. The LDH-derived catalysts of the invention are active in the hydrogenation of $CO_2$ to methanol, and show (Continued)

improved activity with respect to Cu/ZnO catalysts derived from copper-zinc hydroxycarbonate precursors.

15 Claims, 23 Drawing Sheets

(51) Int. Cl.
    *C07C 29/154*     (2006.01)
    *C07C 31/04*     (2006.01)

(52) U.S. Cl.
    CPC ...... *C01P 2002/22* (2013.01); *C01P 2002/72* (2013.01); *C01P 2002/85* (2013.01); *C01P 2004/04* (2013.01); *C07C 31/04* (2013.01)

(56) References Cited

U.S. PATENT DOCUMENTS

| | | | |
|---|---|---|---|
| 2008/0293957 | A1 | 11/2008 | Winters et al. |
| 2008/0300352 | A1 | 12/2008 | Schomaker et al. |
| 2014/0309102 | A1 | 10/2014 | Basile et al. |
| 2020/0017368 | A1 | 1/2020 | O'Hare et al. |
| 2021/0363025 | A1 | 11/2021 | Wongariyakawee et al. |

FOREIGN PATENT DOCUMENTS

| | | |
|---|---|---|
| CN | 103111627 A | 5/2013 |
| CN | 103965661 A | 8/2014 |
| CN | 104342269 A | 2/2015 |
| CN | 105013492 A | 11/2015 |
| CN | 105562009 A | 5/2016 |
| CN | 106674572 A | 5/2017 |
| GB | 1366357 A | 9/1974 |
| GB | 1366367 A | 9/1974 |
| RU | 2426688 C2 | 8/2011 |
| RU | 2540402 C1 | 2/2015 |
| WO | WO-03/082468 A1 | 10/2003 |
| WO | WO-2006/043352 A1 | 4/2006 |
| WO | WO-2007/065877 A1 | 6/2007 |
| WO | WO-2013/072197 A1 | 5/2013 |
| WO | WO-2013/117957 A2 | 8/2013 |
| WO | WO-2014/051530 A2 | 4/2014 |
| WO | WO-2015/144778 A1 | 10/2015 |
| WO | WO-2016/132143 A1 | 8/2016 |
| WO | WO-2017/009664 A1 | 1/2017 |
| WO | WO-2019/220082 A1 | 11/2019 |

OTHER PUBLICATIONS

Chen et al., Synthesis and characterization of aqueous miscible organic-layered double hydroxide, J. Mater. Chem. A, 2014, 2, 15102-15110 (Year: 2014).*

Alternative Tong, Tong et al., Dramatic effects of Gallium promotion on methanol steam reforming Cu—ZnO catalyst for hydrogen production: formation of 5Å copper clusters from Cu—ZnGaOX, ACS Catal., 2013, 3, 1231-1244 (Year: 2013).*

Behrens et al., "Phase-Pure Cu,Zn,Al Hydrotalcite-like Materials as Precursors for Copper rich Cu/ZnO/Al2O3 Catalysts," Chemistry of Materials, 22: 368-397 (2010).

Burch et al., "Support and Additive Effects in the Synthesis of Methanol over Copper Catalysts," Applied Catalysis, 45: 131-150 (1988).

Burch et al., "The Role of Copper and Zinc Oxide in Methanol Synthesis Catalysts," Journal of the Chemical Society Faraday Transactions, 86(15): 2683-2691 (1990).

Busca et al., "Methanol steam reforming over ex-hydrotalcite Cu—Zn—Al catalysts," Applied Catalysis A: General, 310: 70-78 (2006).

Chinchen et al., "The activity and state of the copper surface in methanol synthesis catalysts," Applied Catalysis, 25(1-2): 101-107 (1986).

Derrouiche et al., "Synthesis and Treatment Parameters for Controlling Metal Particle Size and Composition in Cu/ZnO Materials-First Evidence of Cu3Zn Alloy Formation," Chemistry of Materials, 24(12): 2282-2291 (2012).

Fichtl et al., "Counting of Oxygen Defects versus Metal Surface Sites in Methanol Synthesis Catalysts by Different Probe Molecules," Angewandte Chemie, 53(27): 7043-7047 (2014).

Frost., "Junction effect interactions in methanol synthesis catalysts," Nature, 334: 577-580 (1988).

Gunter et al., "Implication of the microstructure of binary Cu/ZnO catalysts for their catalytic activity in methanol synthesis," Catalysis Letters, 71(1-2): 37-44 (2001).

Hambrock et al., "Nano-Brass: Bimetallic Copper/Zinc Colloids by a Nonaqueous Organometallic Route Using [Cu(OCH (Me)CH2NMe2)2] and Et2Zn as Precursors," Chemistry of Materials, 15: 4217-4222 (2003).

Hansen et al., "Atom-Resolved Imaging of Dynamic Shape Changes in Supported Copper Nanocrystals," Science, 295(5562): 2053-2055 (2002).

Jiao et al., "Effects of structural charges on points of zero charge and intrinsic surface reaction equilibrium constants of Zn—Al and Zn—Al—Fe hydrotalcite-like compounds," Colloids and Surfaces A: Physicochemical and Engineering Aspects, 296(1-3): 62-66 (2007).

Kattel et al., "Active sites for CO2 hydrogenation to methanol on Cu/ZnO catalysts," Science, 355(6331): 1296-1299 (2017).

Klier., "Methanol Synthesis," Advances in Catalysis, 31: Publisher Summary (2 pages)(1982).

Kuld et al., "Quantification of Zinc Atoms in a Surface Alloy on Copper in an Industrial-Type Methanol Synthesis Catalyst," Angewandte Chemie International Edition, 53: 5941-5945 (2014).

Kuld et al., "Quantifying the promotion of Cu catalysts by ZnO for methanol synthesis," Science, 352(6288): 969-974 (2016).

Li et al., "Enhanced CO2 hydrogenation to methanol over CuZn nanoalloy in Ga modified Cu/ZnO catalysts," Journal of Catalysis, 343: 157-167 (2016).

Moulder et al., "Handbook of X-ray Photoelectron Spectroscopy," Published by Perkin-Elmer Corporation, Physical Electronics Division: 260 pages (1992).

Saito., "R&D activities in Japan on methanol synthesis from CO2 and H2," Catalysis Surveys from Japan, 2: 175-184 (1998).

Sanches et al., "Influence of preparation methods and Zr and Y promoters on Cu/ZnO catalysts used for methanol steam reforming," International Journal of Hydrogen Energy, 37(8): 6572-6579 (2012).

Schumann et al., "Promoting Strong Metal Support Interaction: Doping ZnO for Enhanced Activity of Cu/ZnO:M (M = Al, Ga, Mg) Catalysts," ACS Catalysis, 5(6): 3260-3270 (2015).

Thompson et al., "Beamline I11 at Diamond: A new instrument for high resolution powder diffraction," AIP Review of Scientific Instruments, 80(7): 10 pages (2009).

Toyir et al., "Highly effective conversion of CO2 to methanol over supported and promoted copper-based catalysts: influence of support and promoter," Applied Catalysis B: Environmental, 29(3): 207-215 (2001).

Van Den Berg et al., "Structure sensitivity of Cu and CuZn catalysts relevant to industrial methanol synthesis," Nature Communications, 7: Article 13057 (2016).

Van Helden et al., "The size-dependent site composition of FCC cobalt nanocrystals," Catalysis Today, 261: 48-59 (2016).

Wang et al., "Recent Advances in the Synthesis and Application of Layered Double Hydroxide (LDH) Nanosheets," Chemical Reviews, 112(7): 4124-4155 (2012).

Zhang et al., "Copper-containing mixed metal oxides derived from layered precursors: control of their compositions and catalytic properties," Journal of Materials Science, 43: 237-243 (2008).

Zhang et al., "Structure and surface characteristics of Cu-based composite metal oxides derived from layered double hydroxides," Materials Chemistry and Physics, 87(2-3): 402-410 (2004).

Kolesnikov et al., "I.M. Kolesnikov, Kataliz v gazoneftyanoy otrasli (Catalysis in the Gas-Oil Industry)," Moscow, 2012, p. 1-472 w/ English Abstract.

(56) References Cited

OTHER PUBLICATIONS

Kolesnikov et al., "Tvyordye katalizatory, ikh struktura, sostav I kataliticheskaya aktivnost (Solid Catalysts, Their Structure, Composition, and Catalytic Activity)," Monograph 1 I.M. Kolesnikov, G.I. Vyakhirev, M.Yu. Kilyanov, V.A. Vinokurov, S.I. Kolesnikov—M.: GUP Izdatelstvo Neft i Gaz publisher, I.M. Gubkin National University of Oil and Gas, 2000.—p. 10 w/ English Abstract.

Chen et al., "Synthesis and characterisation of aqueous miscible organic-layered double hydroxides," Journal of Materials Chemistry A, 2(36): 15102-15110 (2014).

Erastova et al., "Understanding surface interactions in aqueous miscible organic solvent treated layered double hydroxides," RSC Advances, 7(9):5076-5083 (2017).

Gao et al., "Yttrium oxide modified Cu/ZnO/Al 2 O 3 catalysts via hydrotalcite-like precursors for CO 2 hydrogenation to methanol," Catalysis Science & Technology, 5(9):4365-4377 (2015).

Great Britain Search Report for GB Application No. GB1703558.5 dated Aug. 22, 2017.

International Search Report and Written Opinion for International Application No. PCT/GB2018/050567 dated May 16, 2018.

Li et al., "the remarkable activity and stability of a highly dispersive beta-brass Cu—Zn catalyst for the production of ethylene glycol," Scientific Reports, 6(1):6 (2016).

Tong et al., "Direct methanol steam reforming to hydrogen over CuZnGa0x catalysts without CO post-treatment: mechanistic considerations," Physical Chemistry Chemical Physics, 15(19):7240-7240 (2013).

Tong et al., "Dramatic Effects of Gallium Promotion on Methanol Steam Reforming Cu—ZnO Catalyst for Hydrogen Production: Formation of 5 A Copper Clusters from CuZnGa0 x," ACS Catalysis, 3(6):1231-1244 (2013).

Yang et al., "Synthesis and characterisation of layered double hydroide dispersions in organic solvents," RSC Adv, 4(93):51676-51682 (2014).

Extended European Search Report for EP Application No. 18172128 dated Sep. 13, 2018.

International Search Report and Written Opinion for International Application No. PCT/GB2019/051296 dated Jun. 21, 2019.

\* cited by examiner

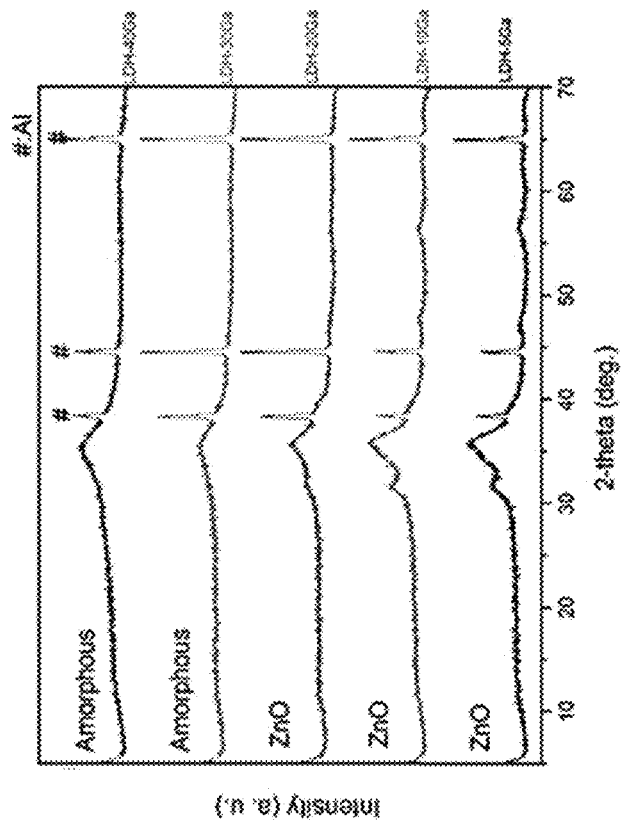
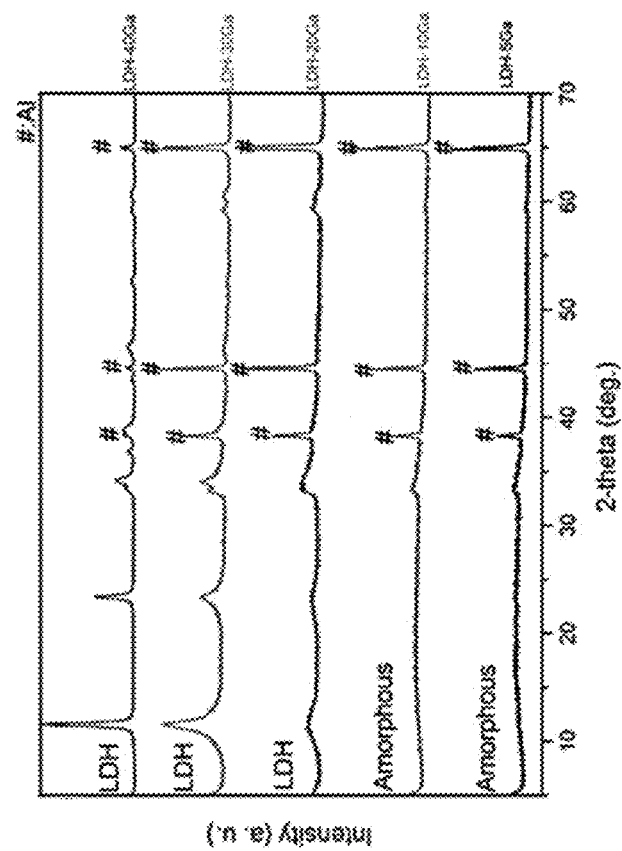
FIG. 3(c)
FIG. 3(d)

Calcined

Reduced
Particle size 5nm~10nm

Calcined

Reduced Particle size <5nm

LAYERED DOUBLE HYDROXIDE PRECURSOR, THEIR PREPARATION PROCESS AND CATALYSTS PREPARED THEREFROM

RELATED APPLICATIONS

This application is the U.S. National Stage Application of PCT/GB2018/050567, filed Mar. 6, 2018, which claims the benefit of priority to United Kingdom Application Ser. No. 1703558.5, filed Mar. 6, 2017.

INTRODUCTION

The present invention relates to new layered double hydroxide materials useful as intermediates in the formation of catalysts, as well as to methods of preparing the layered double hydroxides. The present invention also relates to catalysts suitable for catalysing the hydrogenation of $CO_2$ to methanol, as well as to methods of preparing the catalysts. The present invention also relates to a process of hydrogenating $CO_2$ to methanol using the catalysts.

BACKGROUND OF THE INVENTION

Due to increasing emissions by the ever-expanding global human population, the concentration of $CO_2$ in the atmosphere is rising year on year, and is widely accepted to be a key contributor in global climate change. Attempts to reduce $CO_2$ emissions are plentiful, as are $CO_2$ capture and transformation technologies. It has recently been demonstrated that by utilizing solar energy, wind power, hydropower and biomass, renewable hydrogen gas can be produced on a large scale[1,2]. Therefore, the recycling of $CO_2$ through its hydrogenation to high-energy-content fuels such as alcohols or hydrocarbons appears to be very attractive[3].

The hydrogenation of $CO_2$ to methanol has attracted significant interest due to the value of methanol, both as a chemical platform and a clean fuel. Compounds able to effectively catalyse the conversion of $CO_2$ to methanol are therefore becoming increasingly attractive.

Cu/ZnO-based catalysts are known to be active in the catalytic hydrogenation of either CO or $CO_2$ to methanol. Within such Cu/ZnO-based catalysts, the surface of Cu is generally accepted to provide catalytic active sites, although the role(s) of the ZnO support is still not clear[4-11]. It has also been reported that the incorporation of different additives, such as $Al_2O_3$, $ZrO_2$, $SiO_2$ and $Ga_2O_3$ can further improve the activity, stability and thermal resistance compared with the unmodified Cu/ZnO catalyst[12-17]. Recently, using atom probe tomography technique, stable Cu-containing small and active crystallites (~0.5-2 nm) can be identified in the working catalyst prepared from $Ga^{3+}$ modified Cu/ZnO[18-20]. The formation of $ZnGa_2O_4$ spinel structure is believed to enhance the generation of extremely small Cu clusters under methanol synthesis conditions.

In spite of the advances made with Cu/ZnO-based catalysts, there remains a need for improved catalysts capable of catalyzing the hydrogenation of $CO_2$ to methanol.

The present invention was devised with the foregoing in mind.

SUMMARY OF THE INVENTION

According to a first aspect of the present invention there is provided a layered double hydroxide of formula (I) shown below:

$$[M_{1-x}M'_x(OH)_2]^{a+}(X^{n-})_{a/n} \cdot bH_2O \cdot c(\text{solvent}) \qquad (I)$$

wherein
M is a mixture of divalent cations comprising $Cu^{2+}$ and $Zn^{2+}$;
M' is at least one trivalent cation;
$0<x\leq 0.4$;
$0<b\leq 10$;
$0<c\leq 10$;
X is at least one anion;
n is the charge on anion X and has a value of 1 or 2;
$0.2\leq a\leq 0.4$; and
the solvent is at least one organic solvent capable of hydrogen-bonding to water.

According to a second aspect of the present invention there is provided a process for the preparation of a layered double hydroxide according to the first aspect of the present invention, the process comprising the steps of:
a) providing a water-washed, wet precipitate of formula (II) shown below, said precipitate having been formed by contacting aqueous solutions containing cations of the metals M and M', the anion(s) $X^{n-}$, and then ageing the reaction mixture:

$$[M_{1-x}M'_x(OH)_2]^{a+}(X^{n-})_{a/n} \cdot bH_2O \qquad (II)$$

wherein M, M', x, a, n, b and X are as defined for formula (I);
b) contacting the water-washed, wet precipitate of step a) with a solvent as defined for formula (I).

According to a third aspect of the present invention there is provided a layered double hydroxide obtainable, obtained or directly obtained by a process according to the second aspect of the present invention.

According to a fourth aspect of the present invention there is provided a thermally-treated layered double hydroxide, wherein the thermally-treated layered double hydroxide is a thermally-treated form of a layered double hydroxide according to the first or third aspect of the present invention.

According to a fifth aspect of the present invention there is provided a process for the preparation of a thermally-treated layered double hydroxide according to the fourth aspect of the invention, the process comprising the steps of:
a) providing a layered double hydroxide according to the first or third aspect of the present invention; and
b) thermally treating the layered double hydroxide of step a).

According to a sixth aspect of the present invention there is provided a thermally-treated layered double hydroxide obtainable, obtained or directly obtained by a process according to the fifth aspect of the present invention.

According to a seventh aspect of the present invention there is provided a catalyst being a reduced form of a thermally-treated layered double hydroxide according to the fourth or sixth aspect of the present invention.

According to an eighth aspect the present invention provides a catalyst comprising Cu, Zn and Ga in a weight ratio of 1:(0.30-1.30):(0.05-0.75), and wherein the catalyst has a specific surface area of Cu ($S_{Cu}$) of >48 $m^2g^{-1}$.

According to an ninth aspect of the present invention there is provided a process for the preparation of a catalyst, the process comprising the steps of:
a) providing a thermally-treated layered double hydroxide according to the fourth or sixth aspect of the present invention; and
b) reducing the thermally-treated layered double hydroxide provided in step a).

According to a tenth aspect of the present invention there is provided a catalyst obtainable, obtained or directly obtained by a process according to the seventh aspect of the present invention.

According to a eleventh aspect of the present invention there is provided a process for the preparation of methanol by hydrogenation of carbon dioxide and/or carbon monoxide, the process comprising the step of:
a) contacting a catalyst according to the seventh or ninth aspect of the present invention with a mixture of hydrogen and one or both of carbon monoxide and carbon dioxide.

BRIEF DESCRIPTION OF THE FIGURES

FIG. 3(c) shows XRD profiles of freshly prepared LDH pre-catalyst.

FIG. 3(d) shows XRD profiles of calcined LDH pre-catalyst at 330° C.

FIG. 5(g) shows the LDH30Ga structural model showing 3 cationic layers with intercalated carbonate anions and water molecules in between.

DETAILED DESCRIPTION OF THE INVENTION

Layered Double Hydroxides of the Invention

Figure 1:
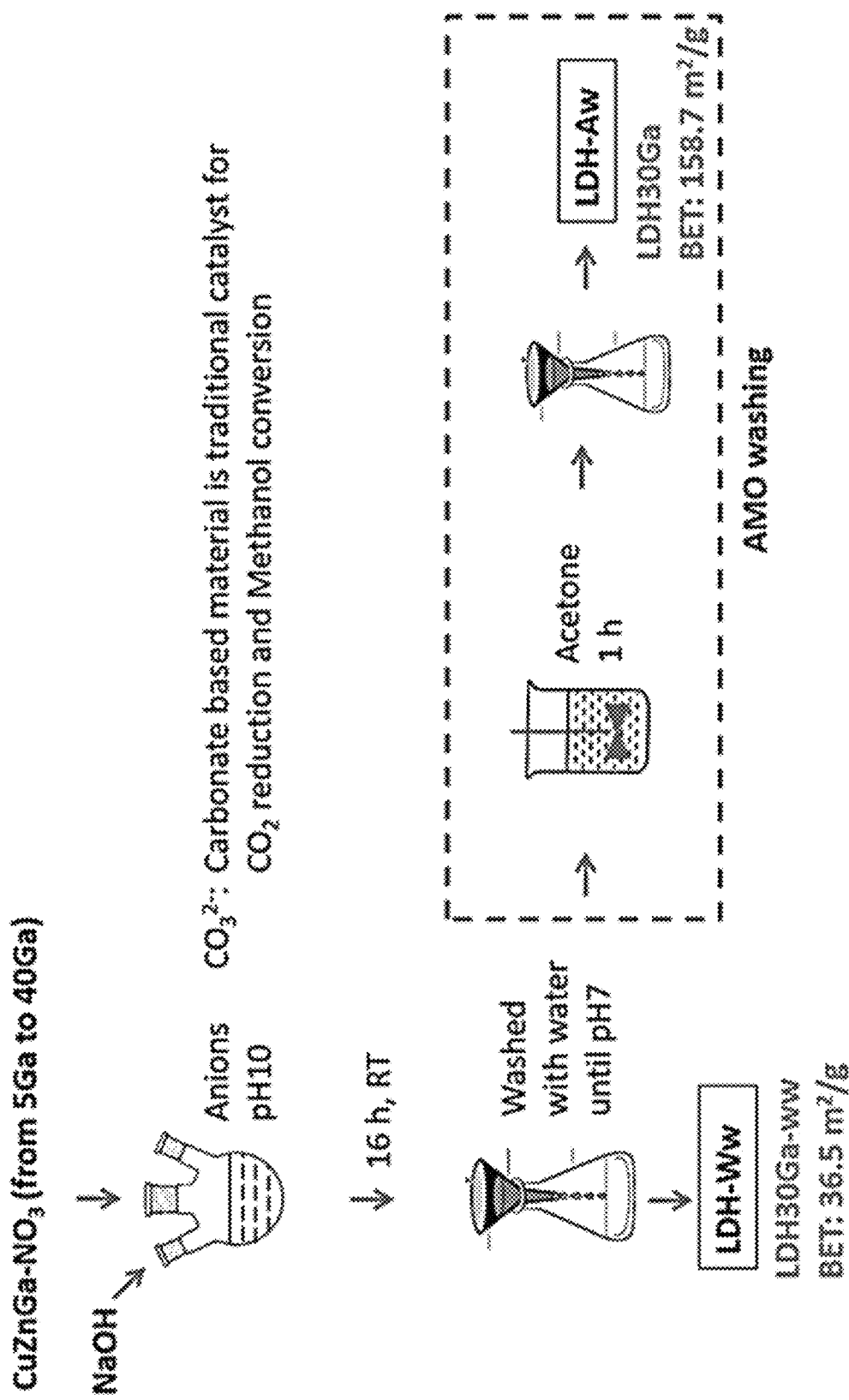
FIG. 1 shows the procedure for the synthesis of LDH samples via base solution.

As described hereinbefore, in a first aspect the present invention provides a layered double hydroxide of formula (I) shown below:

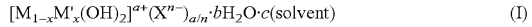

$$[M_{1-x}M'_x(OH)_2]^{a+}(X^{n-})_{a/n} \cdot bH_2O \cdot c(\text{solvent}) \qquad (I)$$

wherein
M is a mixture of divalent cations comprising $Cu^{2+}$ and $Zn^{2+}$;
M' is at least one trivalent cation;
$0<x\leq0.4$;
$0<b\leq10$;
$0<c\leq10$;
X is at least one anion;
n is the charge on anion X and has a value of 1 or 2;
$0.2\leq a\leq0.4$; and
the solvent is at least one organic solvent capable of hydrogen-bonding to water.

Set against the backdrop of Cu/ZnO catalysts prepared from copper-zinc hydroxycarbonate precursors, the inventors have surprisingly found that layered double hydroxides (LDHs) having a structure according to formula (I) can serve as convenient intermediates in the preparation of new catalysts capable of hydrogenating $CO_2$ to methanol. In particular, the LDHs of the invention can be facilely converted into the active catalyst by simple thermal treatment, followed by reduction. When compared with gallium-modified Cu/ZnO catalysts (prepared from hydroxycarbonate precursors), catalysts derived from the LDHs of the invention possess remarkably small Cu crystallites, the surfaces of which serve as active sites in the catalytic hydrogenation of $CO_2$ to methanol. As a consequence, when compared with gallium-modified Cu/ZnO catalysts having comparable Cu loadings, catalysts derived from the LDHs of the invention exhibit improved catalytic activity in the hydrogenation of $CO_2$ to methanol.

In an embodiment, M' is at least one trivalent cation selected from $Al^{3+}$, $Ga^{3+}$, $Y^{3+}$, $In^{3+}$, $Fe^{3+}$, $Co^{3+}$, $Ni^{3+}$, $Mn^{3+}$, $Cr^{3+}$, $Ti^{3+}$, $V^{3+}$ and $La^{3+}$. Suitably, M' is $Ga^{3+}$, and optionally one or more other trivalent cations selected from $Al^{3+}$, $Y^{3+}$, $In^{3+}$, $Fe^{3+}$, $Co^{3+}$, $Ni^{3+}$, $Mn^{3+}$, $Cr^{3+}$, $Ti^{3+}$, $V^{3+}$ and $La^{3+}$. More suitably, M' is $Ga^{3+}$, and optionally one or more other trivalent cations selected from $Al^{3+}$ and $Y^{3+}$. Even more suitably, M' is $Ga^{3+}$, and optionally $Y^{3+}$. Most suitably, M' is $Ga^{3+}$.

Alternatively, M' is $Ga^{3+}$, and optionally one or more other trivalent cations selected from $Y^{3+}$, $In^{3+}$, $Fe^{3+}$, $Co^{3+}$, $Ni^{3+}$, $Mn^{3+}$, $Cr^{3+}$, $Ti^{3+}$, $V^{3+}$ and $La^{3+}$. Suitably, M' is $Ga^{3+}$, and optionally one or more other trivalent cations selected from $In^{3+}$, $Fe^{3+}$, $Co^{3+}$, $Ni^{3+}$, $Mn^{3+}$, $Cr^{3+}$, $Ti^{3+}$, $V^{3+}$ and $La^{3+}$.

In an embodiment, M is a mixture of divalent cations comprising $Cu^{2+}$ and $Zn^{2+}$, as well as one or more other divalent cations selected from $Mg^{2+}$, $Fe^{2+}$, $Ca^{2+}$, $Sn^{2+}$, $Ni^{2+}$, $Co^{2+}$, $Mn^{2+}$ and $Cd^{2+}$. Suitably, M is a mixture of divalent cations consisting of $Cu^{2+}$ and $Zn^{2+}$.

In an embodiment, M' is $Ga^{3+}$ and M is a mixture of divalent cations consisting of $Cu^{2+}$ and $Zn^{2+}$.

In an embodiment, the value of x varies according to the expression $0.05 \leq x \leq 0.35$. Suitably, the value of x varies according to the expression $0.1 \leq x \leq 0.35$. More suitably, the value of x varies according to the expression $0.12 \leq x \leq 0.35$. Even more suitably, the value of x varies according to the expression $0.12 \leq x \leq 0.32$. Even more suitably, the value of x varies according to the expression $0.13 \leq x \leq 0.30$. Even more suitably, the value of x varies according to the expression $0.16 \leq x \leq 0.30$. Even more suitably, the value of x varies according to the expression $0.18 \leq x \leq 1.30$. Most suitably, the value of x varies according to the expression $0.20 \leq x \leq 0.30$.

In an embodiment, the mole ratio of $Cu^{2+}$ to $Zn^{2+}$ ranges from 1:0.20 to 1:20. Suitably, the mole ratio of $Cu^{2+}$ to $Zn^{2+}$ ranges from 1:0.20 to 1:1.50. More suitably, the mole ratio of $Cu^{2+}$ to $Zn^{2+}$ ranges from 1:0.30 to 1:1.20. Even more suitably, the mole ratio of $Cu^{2+}$ to $Zn^{2+}$ ranges from 1:0.40 to 1:15. Even more suitably, the mole ratio of $Cu^{2+}$ to $Zn^{2+}$ ranges from 1:0.50 to 1:1.15. Even more suitably, the mole ratio of $Cu^{2+}$ to $Zn^{2+}$ ranges from 1:0.60 to 1:1.0. Even more suitably, the mole ratio of $Cu^{2+}$ to $Zn^{2+}$ ranges from 1:0.60 to 1:0.95. Most suitably, the mole ratio of $Cu^{2+}$ to $Zn^{2+}$ ranges from 1:0.60 to 1:0.85.

In an embodiment, M is a mixture of divalent cations consisting of $Cu^{2+}$ and $Zn^{2+}$ and the molar ratio of Cu:Zn:M' is 1:(0.30-1.30):(0.05-0.80). Suitably, the molar ratio of Cu:Zn:M' is 1:(0.35-1.20):(0.08-0.75). More suitably, the molar ratio of Cu:Zn:M' is 1:(0.40-1.10):(0.12-0.70). Even more suitably, the molar ratio of Cu:Zn:M' is 1:(0.42-1.00):(0.18-0.65). Yet more suitably, the molar ratio of Cu:Zn:M' is 1:(0.48-0.95):(0.25-0.55). Yet even more suitably, the molar ratio of Cu:Zn:M' is 1:(0.55-0.85):(0.30-0.55).

In an embodiment, M' is $Ga^{3+}$ and M is a mixture of divalent cations consisting of $Cu^{2+}$ and $Zn^{2+}$ and the molar ratio of Cu:Zn:Ga is 1:(0.30-1.30):(0.05-0.80). Suitably, the molar ratio of Cu:Zn:Ga is 1:(0.35-1.20):(0.08-0.75). More suitably, the molar ratio of Cu:Zn:Ga is 1:(0.40-1.10):(0.12-0.70). Even more suitably, the molar ratio of Cu:Zn:Ga is 1:(0.42-1.00):(0.18-0.65). Yet more suitably, the molar ratio of Cu:Zn:Ga is 1:(0.48-0.95):(0.25-0.55). Yet even more suitably, the molar ratio of Cu:Zn:Ga is 1:(0.55-0.85):(0.30-0.55).

In a particularly suitable embodiment, M' is $Ga^{3+}$ and M is a mixture of divalent cations consisting of $Cu^{2+}$ and $Zn^{2+}$ and the molar ratio of Cu:Zn:Ga is 1:(0.62-0.72):(0.40-0.50).

In an embodiment, X is at least one anion selected from a halide, an inorganic oxyanion, or an organic anion. Suitable halides include chloride. Suitable inorganic oxyanions include carbonate, bicarbonate, hydrogenphosphate, dihydrogenphosphate, nitrite, borate, nitrate, phosphate and sulphate. Suitable organic anions include anionic surfactants and anionic chromophores.

In an embodiment, X is at least one inorganic oxyanion selected from carbonate, bicarbonate, hydrogenphosphate, dihydrogenphosphate, nitrite, borate, nitrate, sulphate and phosphate. Suitably, X is carbonate.

The solvent of formula (I) may have any suitable hydrogen bond donor and/or acceptor groups. Exemplary hydrogen bond donor groups include R—OH, R—$NH_2$, $R_2$NH, whereas exemplary hydrogen bond acceptor groups include ROR, $R_2$C=O $RNO_2$, $R_2$NO, $R_3$N, R—OH, R—$CF_3$.

In an embodiment, the solvent of formula (I) is at least one solvent selected from acetone, acetonitrile, dimethylformamide, dimethyl sulphoxide, dioxane, ethanol, methanol, n-propanol, isopropanol, tetrahydrofuran, ethyl acetate, n-butanol, sec-butanol, n-pentanol, n-hexanol, cyclohexanol, diethyl ether, diisopropyl ether, di-n-butyl ether, methyl tert-butyl ether (MTBE), tert-amyl methyl ether, cyclopentyl methyl ether, cyclohexanone, methyl ethyl ketone (MEK), methyl isobutyl ketone (MIBK), methyl isoamyl ketone, methyl n-amyl ketone, furfural, methyl formate, methyl acetate, isopropyl acetate, n-propyl acetate, isobutyl acetate, n-butyl acetate, n-amyl acetate, n-hexyl acetate, methyl amyl acetate, methoxypropyl acetate, 2-ethoxyethyl acetate and nitromethane. Suitably, the solvent of formula (I) is at least one solvent selected from acetone, acetonitrile and ethanol. More suitably, the solvent of formula (I) is acetone.

In an embodiment, b has a value according to the expression $0 < b \leq 7.5$. Suitably, b has a value according to the expression $0 < b \leq 5$. More suitably, b has a value according to the expression $0 < b \leq 3$.

In another embodiment, c has a value according to the expression $0 < c \leq 7.5$. Suitably, c has a value according to the expression $0 < c \leq 5$. More suitably, c has a value according to the expression $0 < c \leq 1$. Most suitably, c has a value according to the expression $0 < c \leq 0.5$.

In an embodiment, the LDH has a BET surface area of $>100$ $m^2g^{-1}$. Suitably, the LDH has a BET surface area of 100-200 $m^2g^{-1}$.

The LDHs of the invention may be referred to in the accompanying Examples as AMO-LDHs.

Preparation of LDHs of the Invention

As described hereinbefore, in a second aspect the present invention provides a process for the preparation of a layered double hydroxide according to the first aspect of the present invention, the process comprising the steps of:

a) providing a water-washed, wet precipitate of formula (II) shown below, said precipitate having been formed by contacting aqueous solutions containing cations of the metals M and M', the anion(s) $X^{n-}$, and then ageing the reaction mixture:

$[M_{1-x}M'_x(OH)_2]^{a+}(X^{n-})_{a/n} \cdot bH_2O$     (II)

wherein M, M', x, a, n, b and X are as defined for formula (I);

b) contacting the water-washed, wet precipitate of step a) with a solvent as defined for formula (I).

It will be appreciated that M, M', x, a, n, b and X may have any of the definitions appearing hereinbefore in relation to the first aspect of the invention.

The water-washed, wet precipitate of formula (II) may be described as a wet cake.

In an embodiment, step a) comprises the following steps:
a-i) precipitating a layered double hydroxide having the formula (II) from an aqueous solution containing cations of the metals;
a-ii) ageing the layered double hydroxide precipitate obtained in step (a-i) in the reaction mixture of step (a-i);
a-iii) collecting the aged precipitate resulting from step (a-ii), then washing it with water and optionally a 'solvent' as defined hereinbefore for formula (I); and
a-iv) drying and/or filtering the washed precipitate of step (a-iv) to the point that it is still damp.

In an embodiment, in step (a-i), the precipitate is formed by contacting aqueous solutions containing cations of the metals M and M', and the anion $X^{n-}$, in the presence of a base being a source of $OH^-$ (e.g. NaOH, $NH_4OH$, or a precursor for $OH^-$ formation). Suitably, the base is NaOH.

In an embodiment, in step (a-i), the quantity of base used is sufficient to control the pH of the solution above 6.5 (e.g 6.5-13). Suitably, in step (a-i), the quantity of base used is sufficient to control the pH of the solution at 7.5-13. More suitably, in step (a-i), the quantity of base used is sufficient to control the pH of the solution at 9-11.

In an embodiment, in step (a-ii), the layered double hydroxide precipitate obtained in step (a-i) is aged in the reaction mixture of step (a-i) for a period of 5 minutes to 72 hours at a temperature of 15-180° C. Suitably, in step (a-ii), the layered double hydroxide precipitate obtained in step (a-i) is aged in the reaction mixture of step (a-i) for a period of 2 to 20 hours at a temperature of 15-30° C. The ageing step may be conducted under an atmosphere of nitrogen.

In an embodiment, in step (a-iii), the aged precipitate resulting from step (a-ii) is collected, then washed with water and optionally a solvent as defined hereinbefore for formula (I) (e.g. using a Buchner apparatus under ambient conditions) until the filtrate has a pH in the range of 6.5-7.5.

Step b) may be referred to in the accompanying Examples as an AMO washing or AMO treatment step.

In an embodiment, step b) comprises washing the water-washed, wet precipitate of step a) with a solvent as defined for formula (I).

In an embodiment, step b) comprises dispersing the water-washed, wet precipitate of step a) in a solvent as defined for formula (I) to produce a slurry. Suitably, the slurry is maintained for a period of time ranging from 1 minute to 120 hours, during which time aliquots of the solvent may be removed from the slurry and/or fresh aliquots of solvent may be added to the slurry. Suitably, the slurry is stirred whilst being maintained.

In an embodiment, the LDH resulting from step b) is isolated by one or more of filtering, filter pressing, spray drying, cycloning and centrifuging. The isolated LDH may then be dried to give a free-flowing powder. The drying may be performed under ambient conditions, in a vacuum, or by heating to a temperature below 60° C. (e.g. 20 to 60° C.).

Thermally-Treated LDHs of the Invention

As described hereinbefore, in a fourth aspect the present invention provides a thermally-treated form of the LDH according to the first or third aspect of the invention.

Much like the LDHs themselves, thermally-treated forms of the LDHs serve as convenient intermediates in the preparation of new catalysts capable of hydrogenating $CO_2$ to methanol. In particular, the thermally-treated LDHs of the invention can be facilely converted into the active catalyst by simple reduction.

In an embodiment, the thermally-treated LDH has a BET surface area of $>60$ $m^2g^{-1}$. Suitably, the thermally-treated LDH has a BET surface area of 60-150 $m^2g^{-1}$. More suitably, the thermally-treated LDH has a BET surface area of 60-100 $m^2g^{-1}$.

In an embodiment, the thermally-treated LDH is a calcined LDH (i.e. the product of calcining an LDH according to the first or third aspect of the invention).

In an embodiment, the thermally-treated LDH is amorphous, optionally containing traces of ZnO phase. The thermally-treated LDH contains no spinel phase.

Preparation of Thermally-Treated LDHs of the Invention

As described hereinbefore, in a fifth aspect the present invention provides a process for the preparation of a thermally-treated layered double hydroxide according to the fourth aspect of the invention, the process comprising the steps of:
a) providing a layered double hydroxide according to the first or third aspect of the present invention; and
b) thermally treating the layered double hydroxide of step a).

In an embodiment, step b) is conducted at a temperature of 200-450° C. Suitably, step b) is conducted at a temperature of 250-400° C. More suitably, step b) is conducted at a temperature of 300-350° C. Suitably step b) is conducted in air.

Catalysts of the Invention

As described hereinbefore, in a seventh aspect the present invention provides a catalyst being a reduced form of a thermally-treated layered double hydroxide according to the fourth or sixth aspect of the present invention.

As described hereinbefore, in an eighth aspect the present invention provides a catalyst comprising Cu, Zn and Ga in a weight ratio of 1:(0.30-1.30):(0.05-0.75), and wherein the catalyst has a specific surface area of Cu ($S_{Cu}$) of >48 $m^2g^{-1}$.

The catalysts of the invention have a number of advantages when compared with conventional Cu/ZnO catalysts prepared from copper-zinc hydroxycarbonate precursors. Perhaps most notably, the LDH-derived catalysts of the invention possess remarkably small Cu crystallites, the surfaces of which serve as active sites in the catalytic hydrogenation of $CO_2$ to methanol. As a consequence, when compared with gallium-modified Cu/ZnO catalysts having comparable Cu loadings, catalysts derived from the LDHs of the invention exhibit improved catalytic activity in the hydrogenation of $CO_2$ to methanol.

The embodiments discussed in the following paragraphs are applicable to the seventh, eighth and tenth aspects of the invention.

In an embodiment, the catalyst comprises Cu, Zn and Ga in a weight ratio of 1:(0.30-1.30):(0.05-0.75). Suitably, the catalyst comprises Cu, Zn and Ga in a weight ratio of 1:(0.45-1.20):(0.10-0.70). More suitably, the catalyst comprises Cu, Zn and Ga in a weight ratio of 1:(0.55-1.05):(0.20-0.65). Even more suitably, the catalyst comprises Cu, Zn and Ga in a weight ratio of 1:(0.60-1.00):(0.30-0.60). Yet more suitably, the catalyst comprises Cu, Zn and Ga in a weight ratio of 1:(0.60-0.90):(0.40-0.60).

In a particularly suitable embodiment, the catalyst comprises Cu, Zn and Ga in a weight ratio of 1:(0.63-0.80):(0.43-0.57).

In an embodiment, the catalyst has a Cu loading of 30-40% by weight relative to the total weight of the catalyst. Suitably, the catalyst has a Cu loading of 31-39% by weight relative to the total weight of the catalyst. More suitably, the catalyst has a Cu loading of 31-37% by weight relative to the total weight of the catalyst. Even more suitably, the catalyst has a Cu loading of 31-35% by weight relative to the total weight of the catalyst.

In an embodiment, the catalyst has a specific surface area of Cu ($S_{Cu}$) determined by $N_2O$ chemisorption of >48 $m^2g^{-1}$. Suitably, $S_{Cu}$ is 48-200 $m^2g^{-1}$. More suitably, $S_{Cu}$ is 48-150 $m^2g^{-1}$. Even more suitably, $S_{Cu}$ is 50-120 $m^2g^{-1}$. Even more suitably, $S_{Cu}$ is 60-120 $m^2g^{-1}$. Even more suitably, $S_{Cu}$ is 70-120 $m^2g^{-1}$. Even more suitably, $S_{Cu}$ is 80-120 $m^2g^{-1}$. Most suitably, $S_{Cu}$ is 90-120 $m^2g^{-1}$.

In an embodiment, the catalyst has a Cu dispersion of >20% (i.e. 20.1-60% or 20.5-50%). Suitably, the catalyst has a Cu dispersion of >22.0%. More suitably, the catalyst has a Cu dispersion of >23%. Even more suitably, the catalyst has a Cu dispersion of >27%. Even more suitably, the catalyst has a Cu dispersion of >30%. Even more suitably, the catalyst has a Cu dispersion of >35%. Most suitably, the catalyst has a Cu dispersion of >40% (e.g. 40.1-60% or 40.1-50%). The Cu dispersion is defined as the ratio of surface Cu atoms to the total Cu atoms.

In an embodiment, the catalyst comprises Cu, Zn and Ga in a weight ratio of 1:(0.45-1.20):(0.10-0.70), and has a specific surface area of Cu ($S_{Cu}$) of >48 $m^2g^{-1}$ and a Cu dispersion of >20% (e.g. 20.1-60%). Suitably, the catalyst comprises Cu, Zn and Ga in a weight ratio of 1:(0.45-1.20):(0.10-0.70).

In an embodiment, the catalyst comprises Cu, Zn and Ga in a weight ratio of 1:(0.55-1.05):(0.20-0.65), and has a specific surface area of Cu ($S_{Cu}$) of 50-150 $m^2g^{-1}$ and a Cu dispersion of >20% (e.g. 20.1-60%). Suitably, the Cu dispersion is >22% (e.g. 22.1-60%).

In an embodiment, the catalyst comprises Cu, Zn and Ga in a weight ratio of 1:(0.60-1.00):(0.30-0.60), and has a specific surface area of Cu ($S_{Cu}$) of 50-150 $m^2g^{-1}$ and a Cu dispersion of >22% (e.g. 22.1-60%). Suitably, $S_{Cu}$ is 60-120 $m^2g^{-1}$.

In an embodiment, the catalyst comprises Cu, Zn and Ga in a weight ratio of 1:(0.60-0.90):(0.40-0.60), and has a specific surface area of Cu ($S_{Cu}$) of 60-120 $m^2g^{-1}$ and a Cu dispersion of >24% (e.g. 24.1-60%). Suitably, the Cu dispersion of >27% (e.g. 27.1-60%).

In an embodiment, the catalyst comprises Cu, Zn and Ga in a weight ratio of 1:(0.60-0.90):(0.40-0.60), and has a specific surface area of Cu ($S_{Cu}$) of 70-120 $m^2g^{-1}$ and a Cu dispersion of >24% (e.g. 24.1-60%). Suitably, the catalyst comprises Cu, Zn and Ga in a weight ratio of 1:(0.63-0.80):(0.43-0.57).

In an embodiment, the catalyst comprises Cu, Zn and Ga in a weight ratio of 1:(0.63-0.80):(0.43-0.57), and has a specific surface area of Cu ($S_{Cu}$) of 70-120 $m^2g^{-1}$ and a Cu dispersion of >27% (e.g. 27.1-60%). Suitably, the Cu dispersion is >30% (e.g. 30.1-60%).

In an embodiment, the catalyst comprises Cu, Zn and Ga in a weight ratio of 1:(0.63-0.80):(0.43-0.57), and has a specific surface area of Cu ($S_{Cu}$) of 80-120 $m^2g^{-1}$ and a Cu dispersion of >27% (e.g. 27.1-60%). Suitably, $S_{Cu}$ is 90-120 $m^2g^{-1}$.

In an embodiment, the catalyst comprises Cu, Zn and Ga in a weight ratio of 1:(0.63-0.80):(0.43-0.57), and has a specific surface area of Cu ($S_{Cu}$) of 80-120 $m^2g^{-1}$ and a Cu dispersion of >30% (e.g. 30.1-60%). Suitably, $S_{Cu}$ is 90-120 $m^2g^{-1}$.

In an embodiment, the catalyst comprises Cu, Zn and Ga in a weight ratio of 1:(0.63-0.80):(0.43-0.57), and has a specific surface area of Cu ($S_{Cu}$) of 80-120 $m^2g^{-1}$ and a Cu dispersion of >35% (e.g. 35.1-60%). Suitably, the Cu dispersion is >40% (e.g. 40.1-60%).

In an embodiment, the catalyst comprises Cu, Zn and Ga in a weight ratio of 1:(0.63-0.80):(0.43-0.57), and has a specific surface area of Cu ($S_{Cu}$) of 90-120 $m^2g^{-1}$ and a Cu dispersion of >35% (e.g. 35.1-60%). Suitably, the Cu dispersion is >40% (e.g. 40.1-60% or 40.1-50%).

In an embodiment, the catalyst has a $Zn^0$ to $Cu^0$ mole ratio of 0.1:1 to 0.4:1. Reduction of the thermally treated LDH may not only reduce $Cu^{2+}$ to $Cu^0$, but may also reduce $Zn^{2+}$ to $Zn^0$. Such quantities of $Zn^0$ are believed to decorate the surface of the Cu crystallites and lead to improved catalytic activity.

In an embodiment, the catalyst comprises Cu particles having a diameter of <5 nm as determined by TEM.

In an embodiment, the catalyst comprises a quantity of $Zn^0$. The quantity of $Zn^0$ may be detectable by X-ray photoelectron spectroscopy.

In an embodiment, the X-ray photoelectron spectrum of the catalyst contains two peaks attributable to Zn species in the range 1018-1025 eV. Suitably, the two peaks relate to $Zn^{2+}$ and $Zn^0$. Suitably, the X-ray photoelectron spectrum of the catalyst contains a peak attributable to $Zn^0$ at 1020.8-1022.0 eV.

In an embodiment, the X-ray photoelectron spectrum of the catalyst contains one or more of the peaks illustrated in FIG. 9.

Preparation of Catalysts of the Invention

As described hereinbefore, in an ninth aspect the present invention provides a process for the preparation of a catalyst, the process comprising the steps of:
a) providing a thermally-treated layered double hydroxide according to the fourth or sixth aspect of the present invention; and
b) reducing the thermally-treated layered double hydroxide provided in step a).

In an embodiment, step b) comprises heating the layered double hydroxide in an atmosphere of hydrogen. Suitably, step b) comprises heating the layered double hydroxide to a temperature of 250-350° C. in an atmosphere of hydrogen. Step b) may be performed for a period of 5 minutes to 10 hours. Suitably, step b) is performed for 1-4 hours.

In an embodiment, step b) comprises contacting the layered double hydroxide with a chemical reducing agent. Any suitable reducing agent may be used. Exemplary reducing agents include hydrazine and sodium borohydride.

In an embodiment, the thermally-treated layered double hydroxide provided in step a) is formed in situ prior to step b) being conducted. In such embodiments, step a) may comprise performing the method steps according to the fifth aspect of the invention (i.e. preparation of the thermally-treated layered double hydroxide) to form the thermally-treated layered double hydroxide in situ, with step b) being performed immediately thereafter (i.e. without prior isolation of the thermally-treated layered double hydroxide).

Catalytic Processes of the Invention.

As described hereinbefore, in a eleventh aspect the present invention provides a process for the preparation of methanol by hydrogenation of carbon dioxide and/or carbon monoxide, the process comprising the step of:
a) contacting a catalyst according to the seventh or ninth aspect of the present invention with a mixture of hydrogen and one or both of carbon monoxide and carbon dioxide.

In an embodiment, step a) comprises contacting a catalyst according to the seventh or ninth aspect of the present invention with a mixture of carbon dioxide and hydrogen.

In an embodiment, in step a), the molar ratio of carbon dioxide to hydrogen in the mixture of carbon dioxide and hydrogen ranges from 1:1 to 1:5. Suitably, in step a), the molar ratio of carbon dioxide to hydrogen ranges from 1:2.5 to 1:3.5.

In an embodiment, step a) is conducted at a temperature of 200-350° C.

In an embodiment, step a) is conducted at a temperature of 220-320° C. Suitably, step a) is conducted at a temperature of 240-300° C. More suitably, step a) is conducted at a temperature of 260-290° C.

In an embodiment, step a) is conducted at a temperature of 250-320° C. Suitably, step a) is conducted at a temperature of 270-310° C. More suitably, step a) is conducted at a temperature of 290-310° C.

In an embodiment, step a) is conducted at a pressure of 25-65 bar. Suitably, step a) is conducted at a pressure of 35-55 bar. More suitably, step a) is conducted at a pressure of 40-50 bar.

In an embodiment, the GHSV (gas hourly space velocity) value (at standard pressure and temperature) for step a) is 14000-20000 mL g$^{-1}$ h$^{-1}$. Suitably, the GHSV value for step a) is 16000-20000 mL g$^{-1}$ h$^{-1}$. More suitably, the GHSV value for step a) is 17000-19000 mL g$^{-1}$ h$^{-1}$.

In an embodiment, the weight time yield (WTY) of the process is >0.35 g$_{MeOH}$ g$_{cat}^{-1}$ h$^{-1}$ (e.g. 0.351-0.70 g$_{MeOH}$ g$_{cat}^{-1}$ h$^{-1}$). Suitably, the weight time yield of the process is >0.45 g$_{MeOH}$ g$_{cat}^{-1}$ h$^{-1}$. More suitably, the weight time yield of the process is >0.50 g$_{MeOH}$ g$_{cat}^{-1}$ h$^{-1}$.

EXAMPLES

Examples of the invention will now be described, for illustrative purposes only, with reference to the accompanying figures, in which:

FIG. 1 shows the procedure for the synthesis of LDH samples via base solution.

Figure 2:
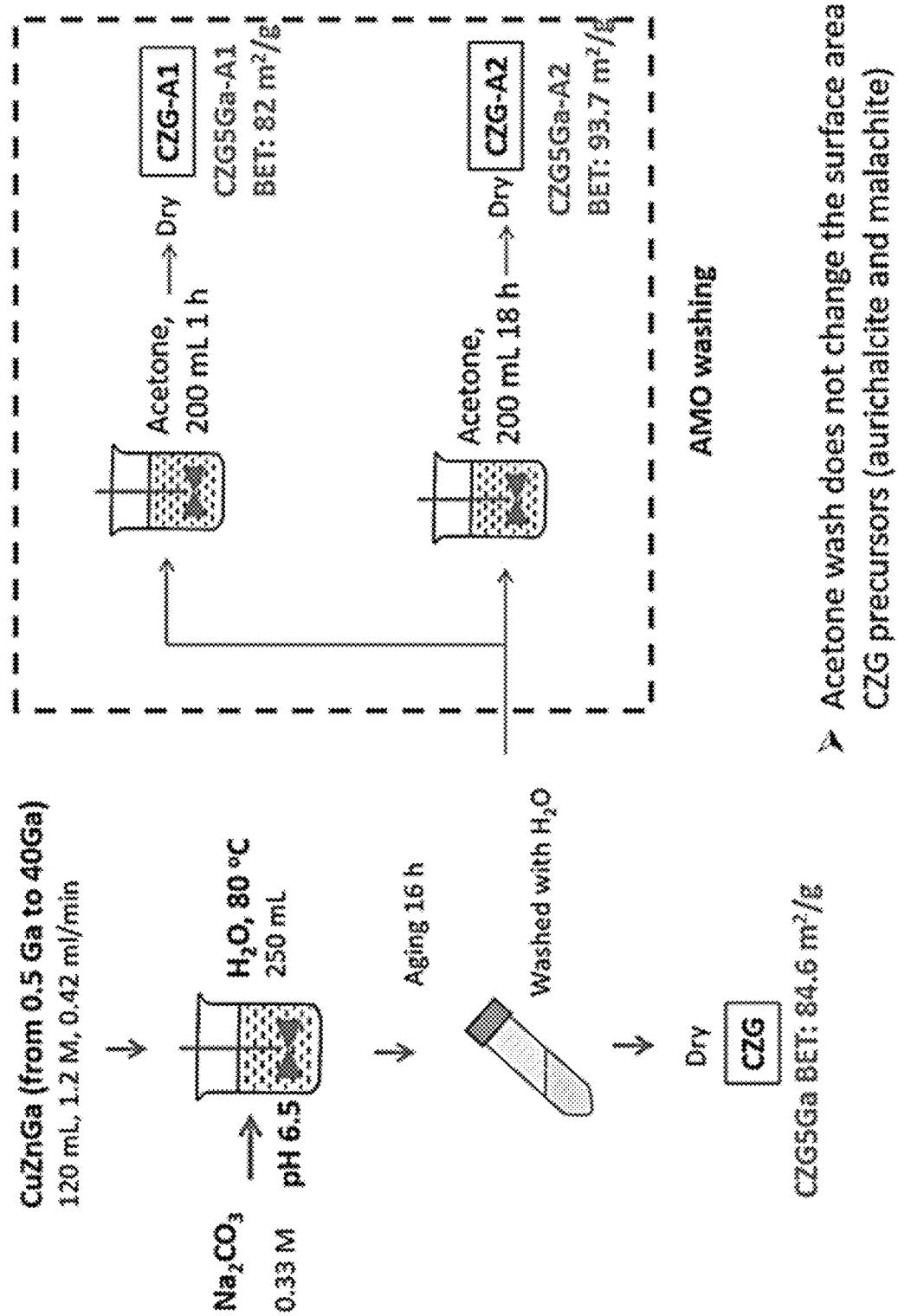
FIG. 2 shows the procedure for the synthesis of CZG samples using co-precipitation.

FIG. 2 shows the procedure for the synthesis of CZG samples using co-precipitation.

Figure 3B:
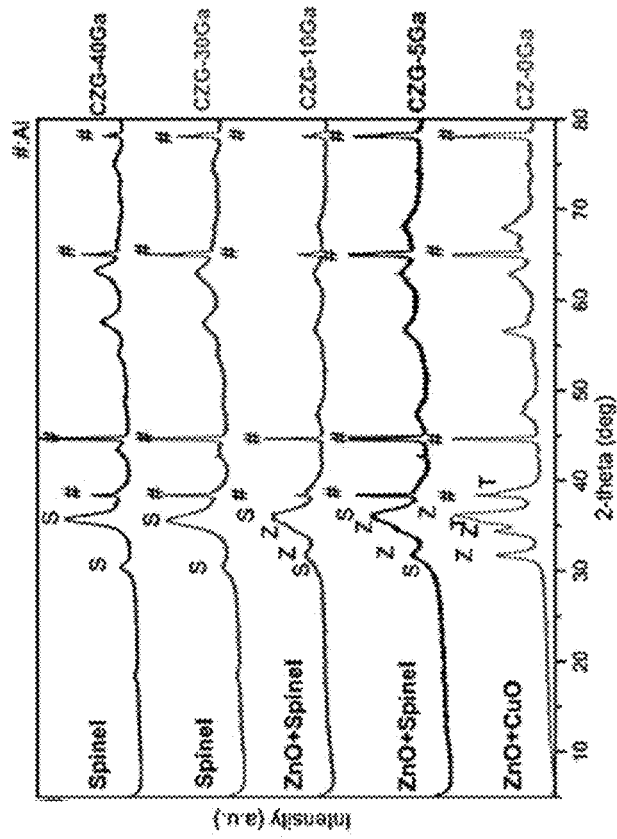
FIG. 3(b) shows XRD profiles of calcined CZG catalyst at 330° C.

FIG. 3 shows XRD profiles of (a) freshly prepared CZG catalyst; (b) calcined CZG catalyst at 330° C.; (c) freshly prepared LDH pre-catalyst; (d) calcined LDH pre-catalyst at 330° C.

Figure 4A:
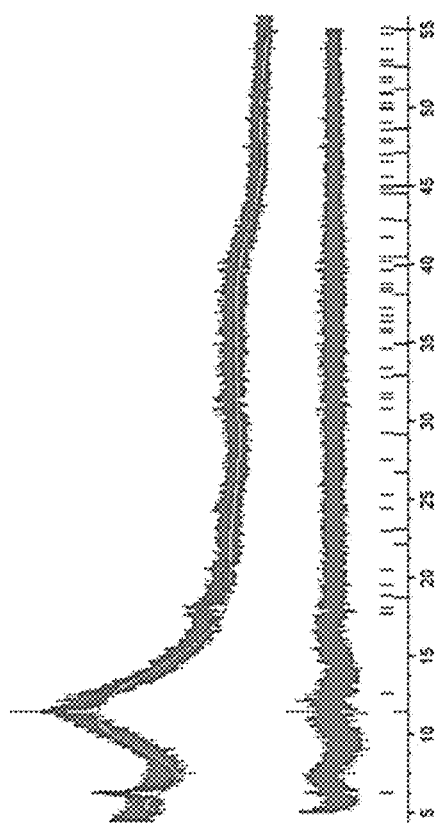
FIG. 4(a) shows SXRD of freshly prepared LDH30Ga by synchrotron XRD (Diamond I11).
Figure 4B:
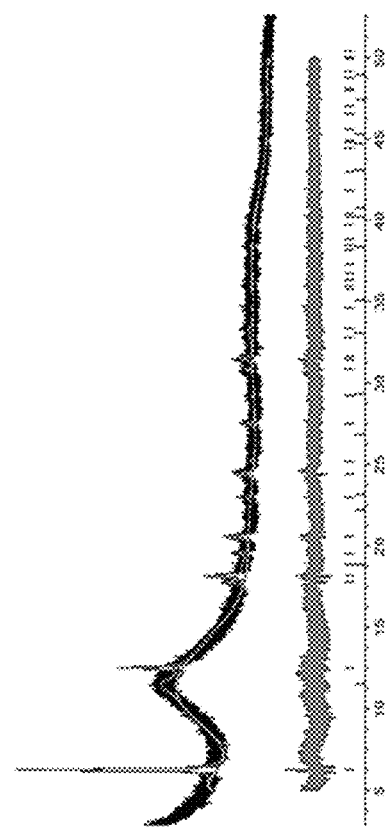
FIG. 4(b) shows SXRD of freshly prepared LDH40Ga by synchrotron XRD (Diamond I11).
Figure 4C:
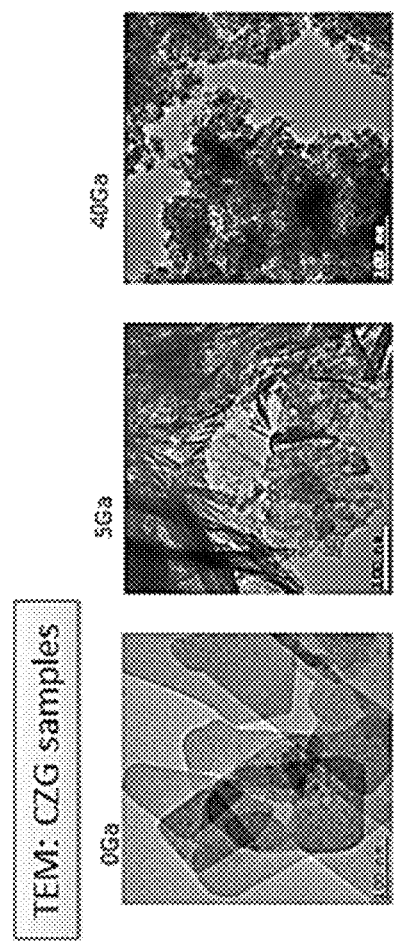
FIG. 4(c) shows TEM images of freshly prepared CZG samples: CZG0Ga (bulk form), CZG5Ga (fibrous-like) and CZG40Ga (small particles).
Figure 4D:
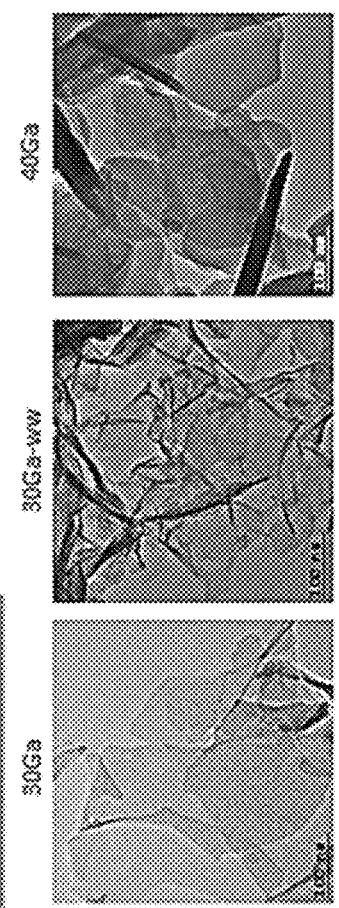
FIG. 4(d) shows TEM images of freshly prepared AMO-LDH samples: LDH30Ga (monolayers), LDH30Ga-ww and LDH40Ga (thick layers).
Figure 4E:
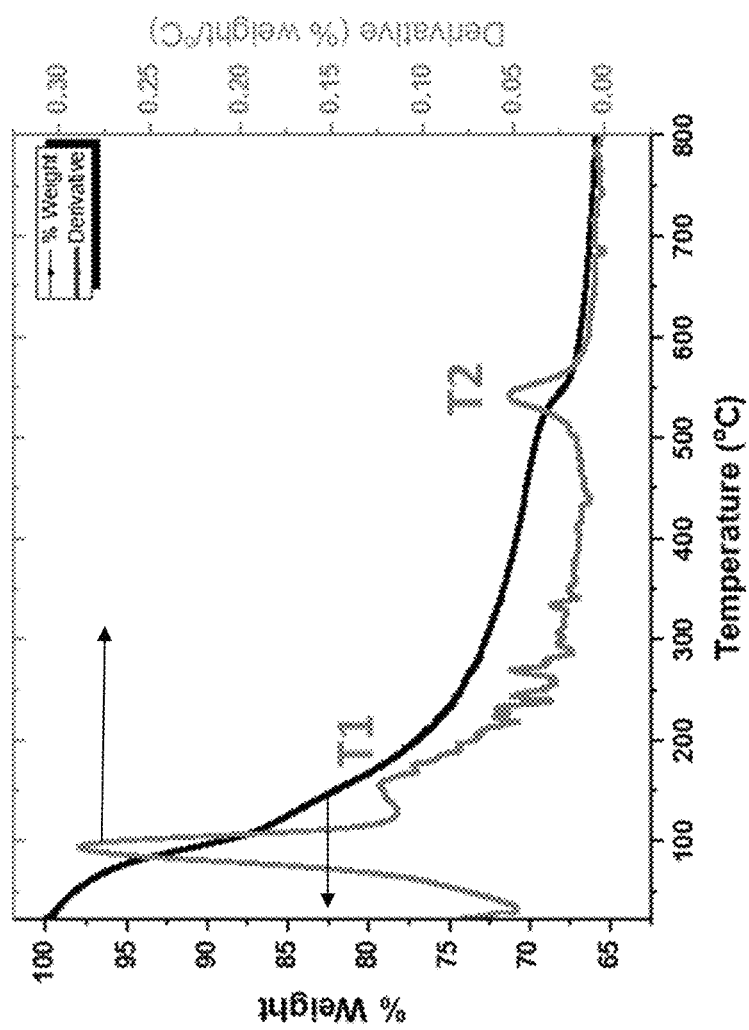
FIG. 4(e) shows thermogravimetric analysis result of the LDH30Ga sample.

FIG. 4a shows SXRD of freshly prepared LDH30Ga by synchrotron XRD (Diamond I11). A best fit model indicates monodispersed spheres with average diameter of 9.48 nm (average ~4 layers): Pawley refinement with the best fitting parameters of r-wp 8.1142; r-exp 6.2624; r-p 6.3235; gof 1.2957. FIG. 4b shows SXRD of freshly prepared LDH40Ga by synchrotron XRD (Diamond I11). Pawley refinement with the best fitting parameters of R$_{wp}$ 7.9297; R$_{exp}$ 5.7502; R$_p$ 6.1762; gof 1.3790. I=27.8994. Monodispersed spheres diameter=4×I÷3=37.16 nm (~46 layers). FIG. 4c shows TEM images of freshly prepared CZG samples: CZG0Ga (bulk form), CZG5Ga (fibrous-like) and CZG40Ga (small particles). FIG. 4d shows TEM images of freshly prepared AMO-LDH samples: LDH30Ga (monolayers), LDH30Ga-ww and LDH40Ga (thick layers). FIG. 4e shows thermogravimetric analysis result of the LDH30Ga sample. T1 and T2: temperature regions at which decomposition of —OH and CO$_3^{2-}$ groups takes place respectively. TGA was performed using a SDT Q600 thermal analyzer. Measurements were performed in the temperature range of 20-800° C. under continuous flow of compressed air (100 mL·min$^{-1}$).

FIG. 5 shows TEM images of freshly-prepared (a) CZG5Ga; (b) CZG40Ga; (c) LDH5Ga and (d) LDH30Ga.

Figure 5A:
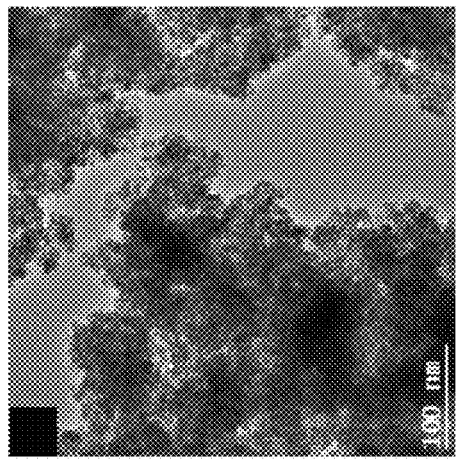
FIG. 5(a) shows TEM images of freshly-prepared CZG5Ga.
Figure 5B:
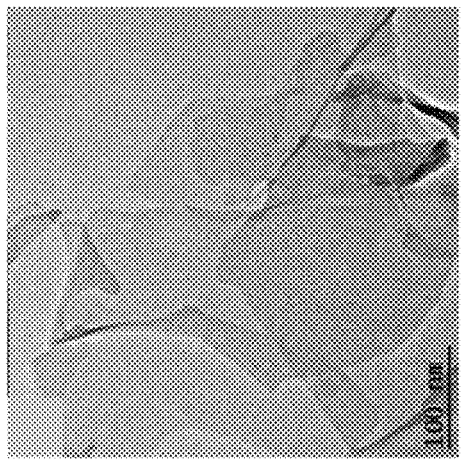
FIG. 5(b) shows TEM images of freshly-prepared CZG40Ga.
Figure 5C:
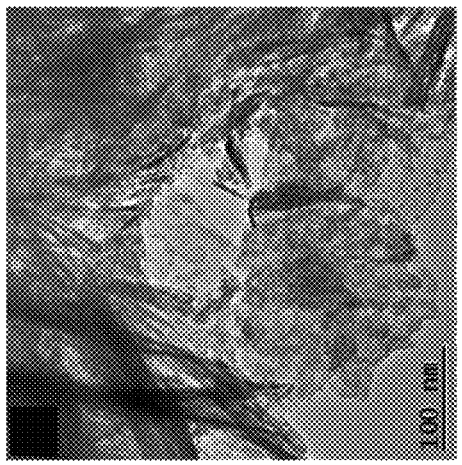
FIG. 5(c) shows TEM images of freshly-prepared LDH5Ga.
Figure 5D:
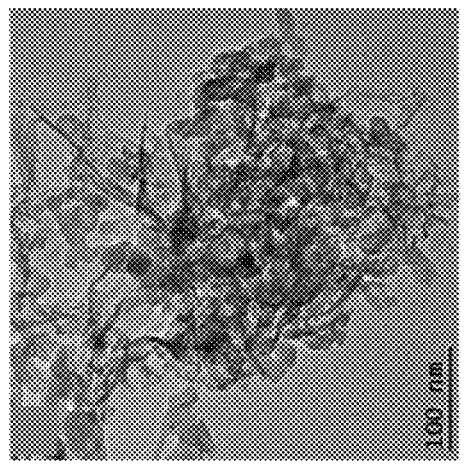
FIG. 5(d) shows TEM images of freshly-prepared LDH30Ga.
Figure 5E:
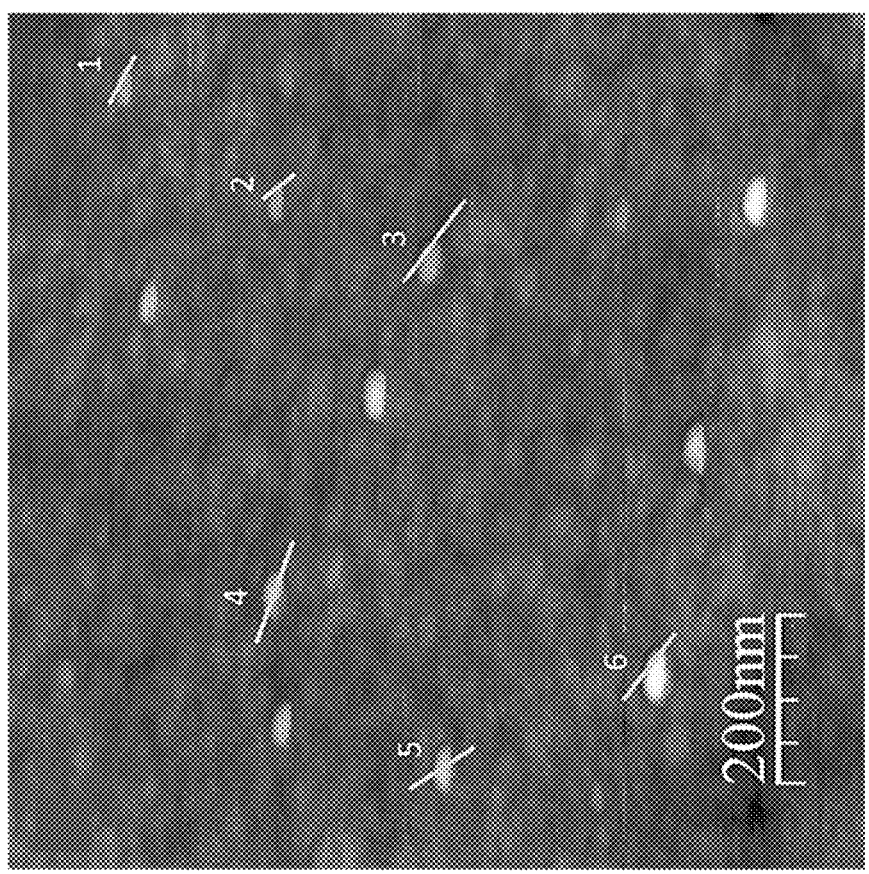
FIG. 5(e) shows AFM image of single layer and few layers freshly prepared LDH30Ga sample on Si substrate.
Figure 5F:
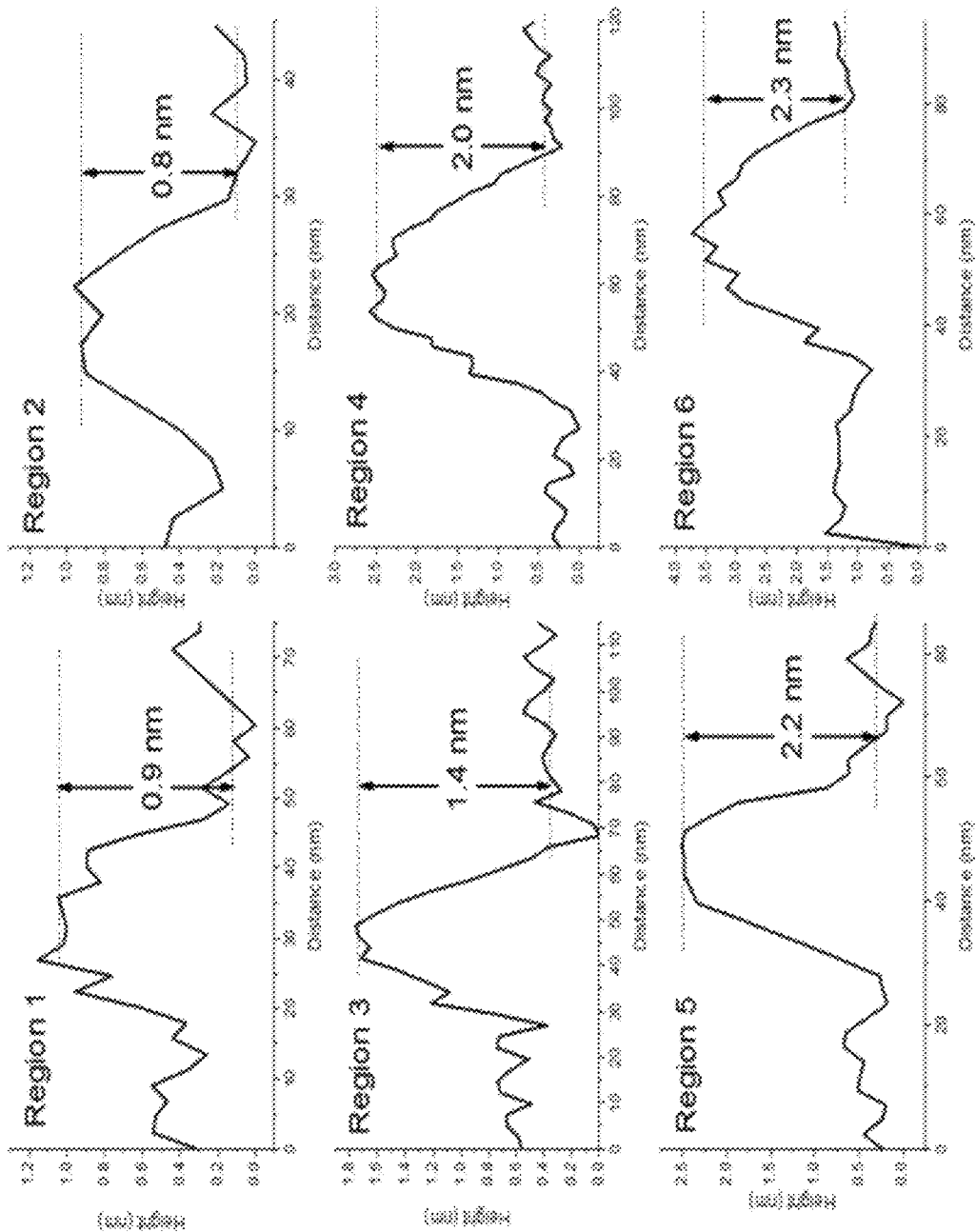
FIG. 5(f) shows the height profile of FIG. 5(e).

FIG. 5e shows AFM image of single layer and few layers freshly prepared LDH30Ga sample on Si substrate. FIG. 5f shows the height profile of FIG. 5e.

Figure 5G:
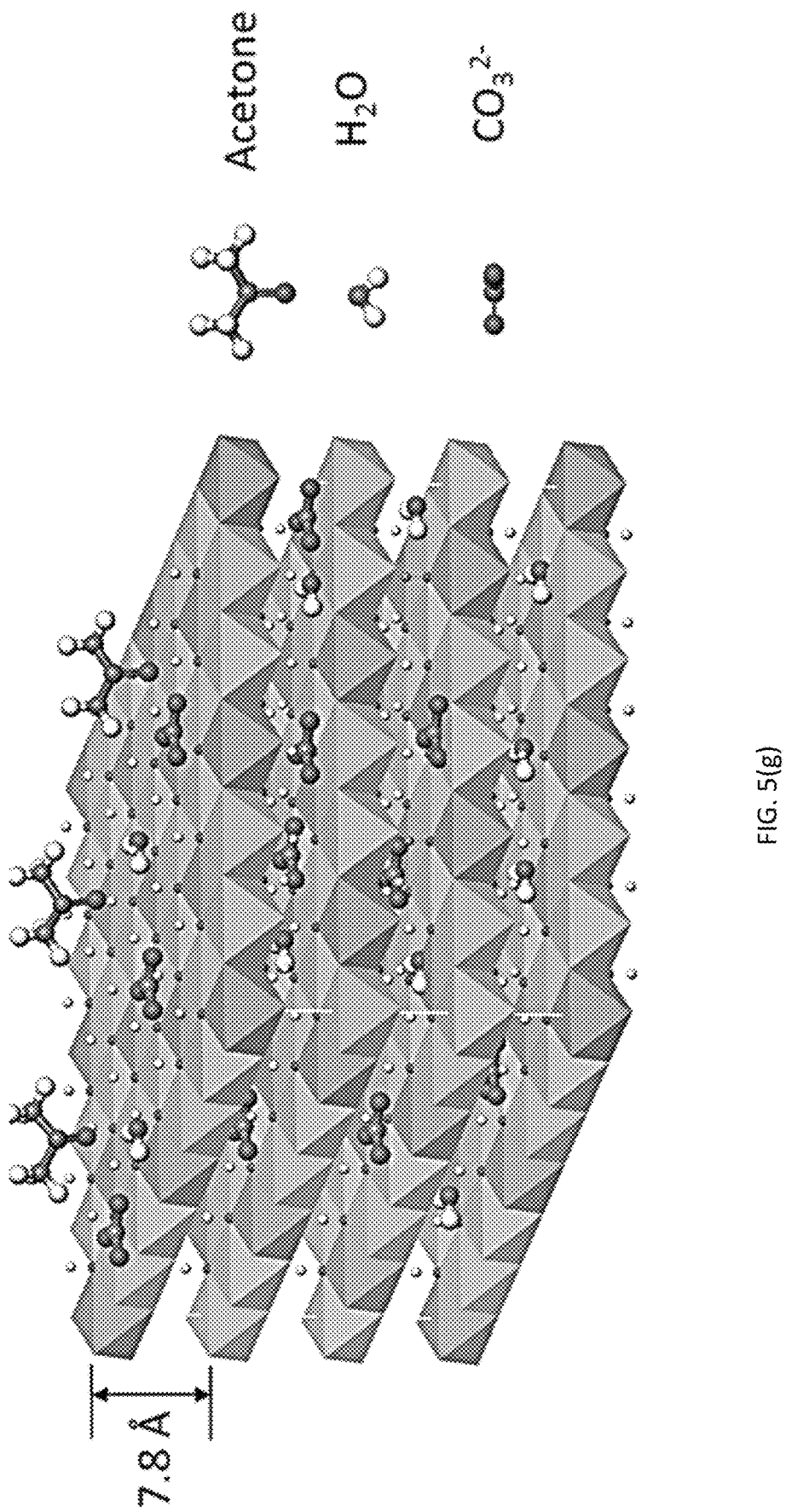

FIG. 5g shows the LDH30Ga structural model showing 3 cationic layers with intercalated carbonate anions and water molecules in between. Each cationic layer contains Cu$^{2+}$ (blue), Zn$^{2+}$ (grey) and Ga$^{3+}$ (orange) with OH$^-$ vertexes in face sharing octahedra with an inter-layer separation of 7.8 Å in a rhombohedral (3R symmetry) [(CuZn)$_{1-x}$Ga$_x$(OH)$_2$] (CO$_3$)$_{x/2}$ LDH structure derived from synchrotron XRD data (FIG. 4a). For simplicity, equal population of Cu, Zn and Ga ions are presented in this model and Jahn-Teller distortion of Cu$^{2+}$ in octahedral sites is also not shown.

Figure 6A:
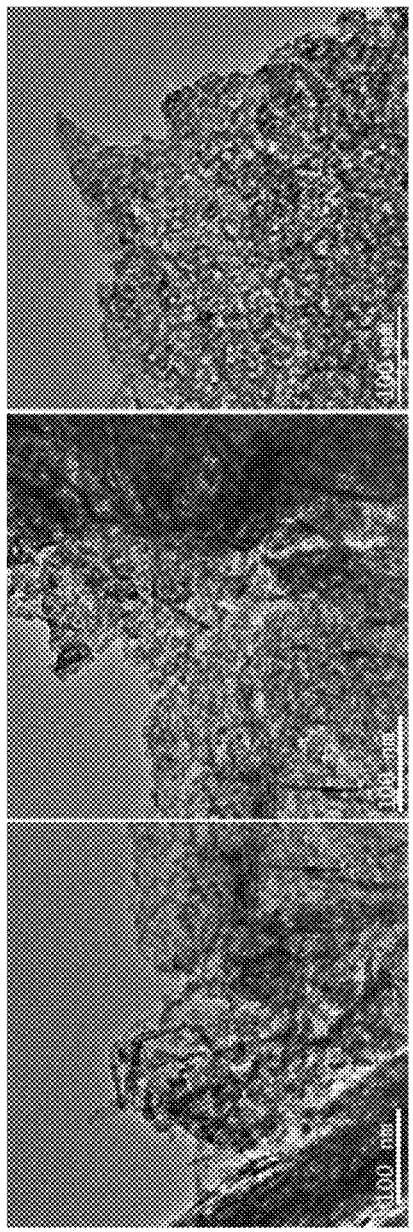
FIG. 6(a) shows TEM images of calcined mixture CZG5Ga.
Figure 6B:
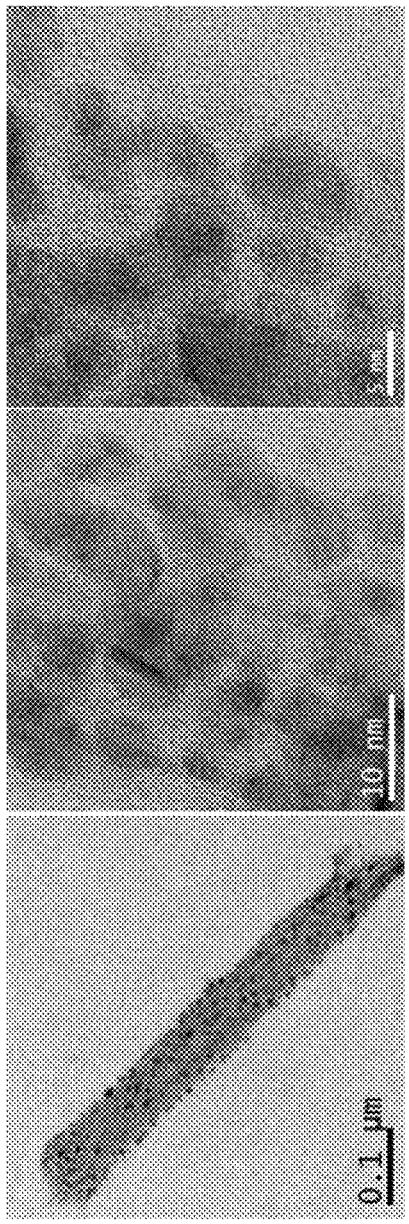
FIG. 6(b) shows TEM images of reduced CZG5Ga containing 5-10 nm Cu/Zn rich particles with some of much larger sizes.
Figure 6C:
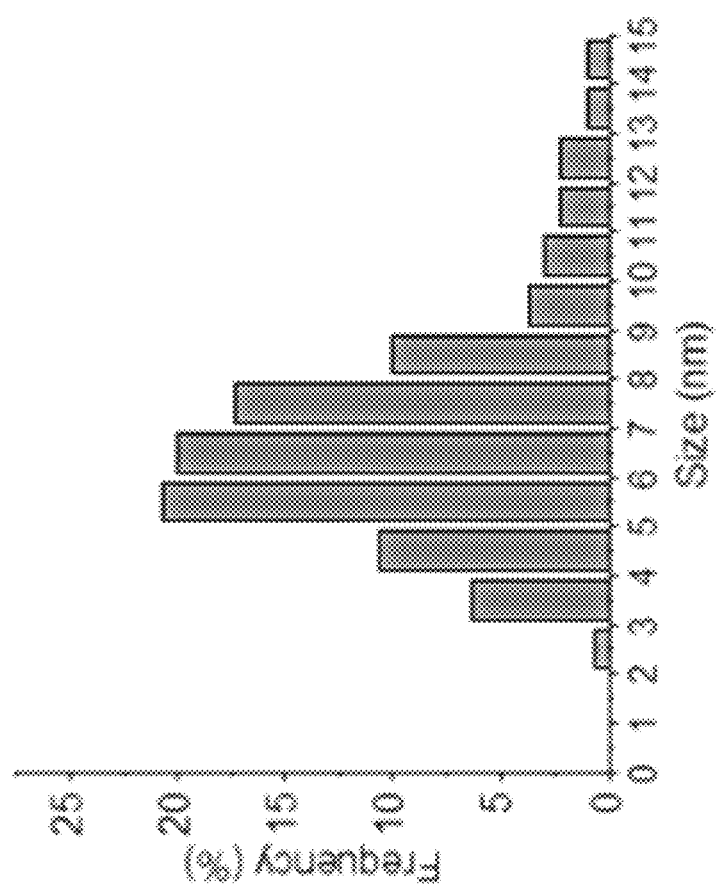
FIG. 6(c) shows the size distribution diagrams of the nanoparticles in the reduced samples.

FIG. 6 shows TEM images, upper rows (a) calcined mixture CZG5Ga; Lower rows (b) reduced CZG5Ga containing 5-10 nm Cu/Zn rich particles with some of much larger sizes. FIG. 6c shows the size distribution diagrams of the nanoparticles in the reduced samples.

Figure 7A:
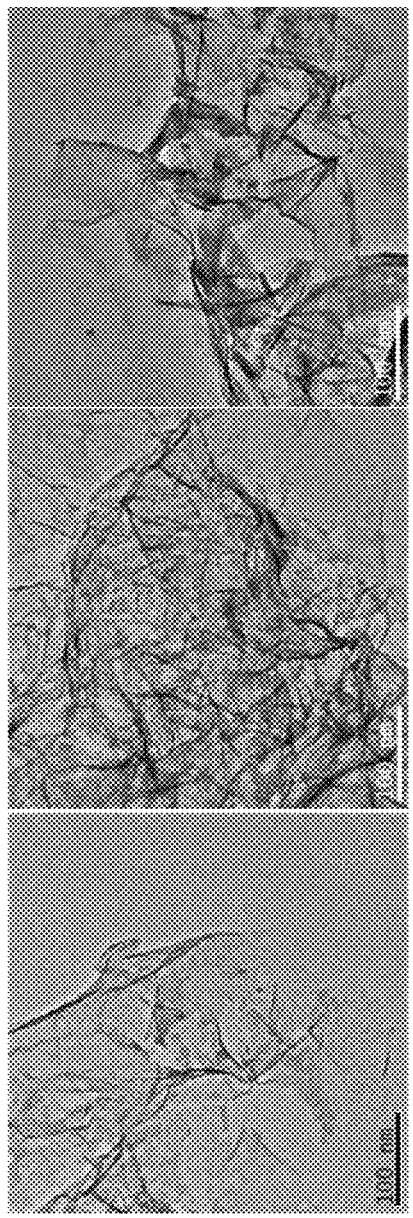
FIG. 7(a) shows TEM images of calcined sheet-like LDH30Ga sample.
Figure 7B:
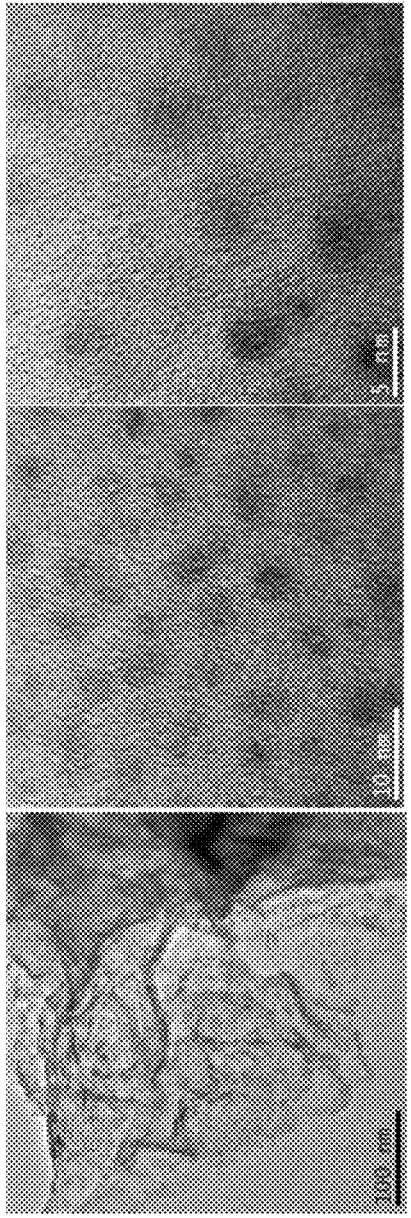
FIG. 7(b) shows TEM images of reduced LDH30Ga containing many homogeneous small Cu/Zn rich particles of <5 nm.
Figure 7C:
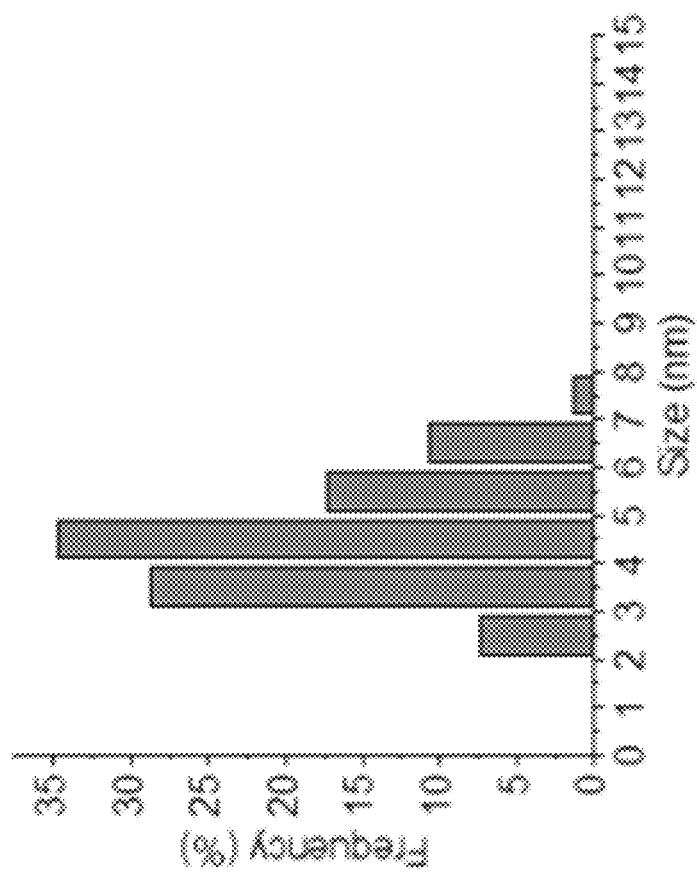
FIG. 7(c) shows the size distribution diagrams of the nanoparticles in the reduced samples.

FIG. 7 shows TEM images, upper rows (a) calcined sheet-like LDH30Ga sample; Lower rows (b) reduced LDH30Ga containing many homogeneous small Cu/Zn rich particles of <5 nm. FIG. 7c shows the size distribution diagrams of the nanoparticles in the reduced samples.

FIG. 8 shows temperature programmed reduction (TPR) profile of (a) CZG samples (b) LDH samples FIG. 9 shows XPS spectra of reduced LDH samples of (a) Ga 2p peaks; (b) Cu 2p peaks; (c) Zn 2 p$_{3/2}$ peaks at various Ga concentrations.

Figure 10:
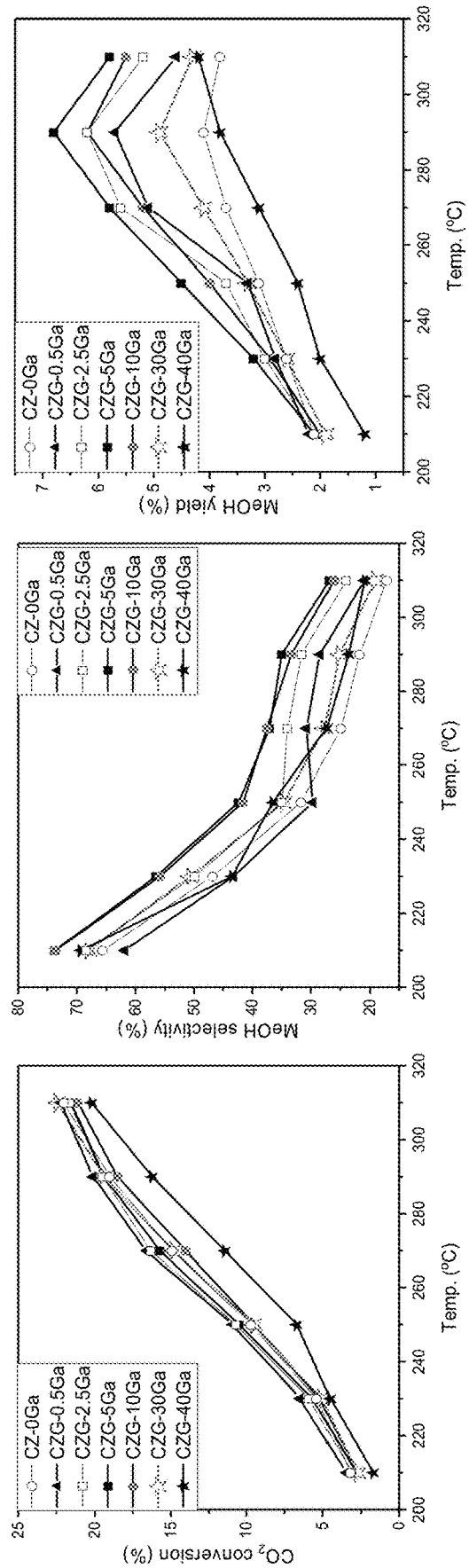
FIG. 10 shows the conversion, selectivity and yield for each CZG samples in $CO_2$ hydrogenation to methanol.

FIG. 10 shows the conversion, selectivity and yield for each CZG samples in CO$_2$ hydrogenation to methanol.

Figure 11:
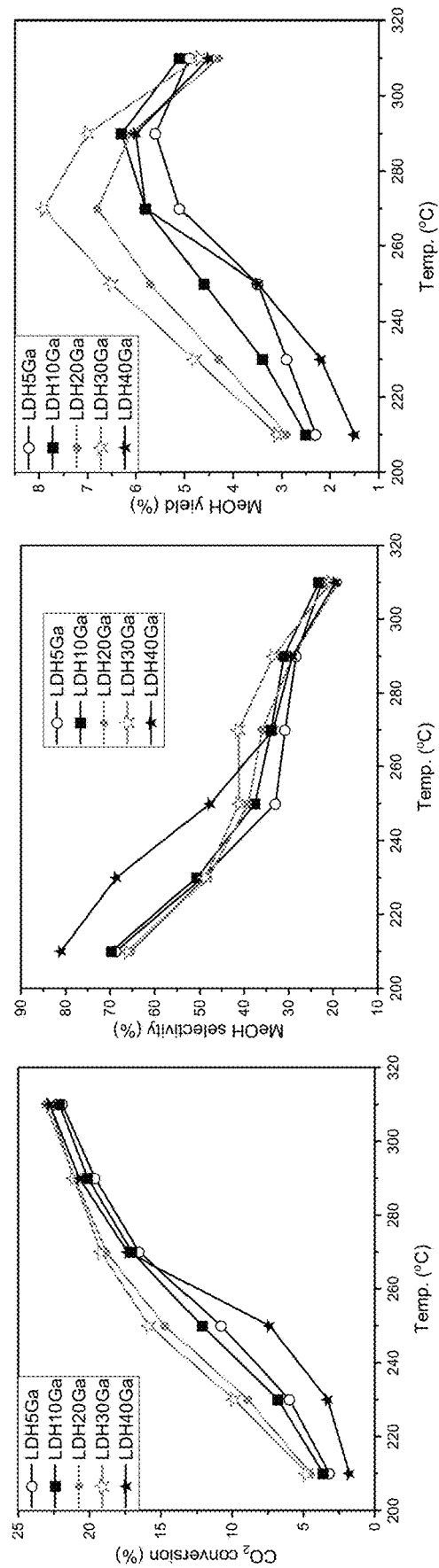
FIG. 11 shows the conversion, selectivity and yield for each LDH samples in $CO_2$ hydrogenation to methanol.

FIG. 11 shows the conversion, selectivity and yield for each LDH samples in CO$_2$ hydrogenation to methanol.

Figure 12:
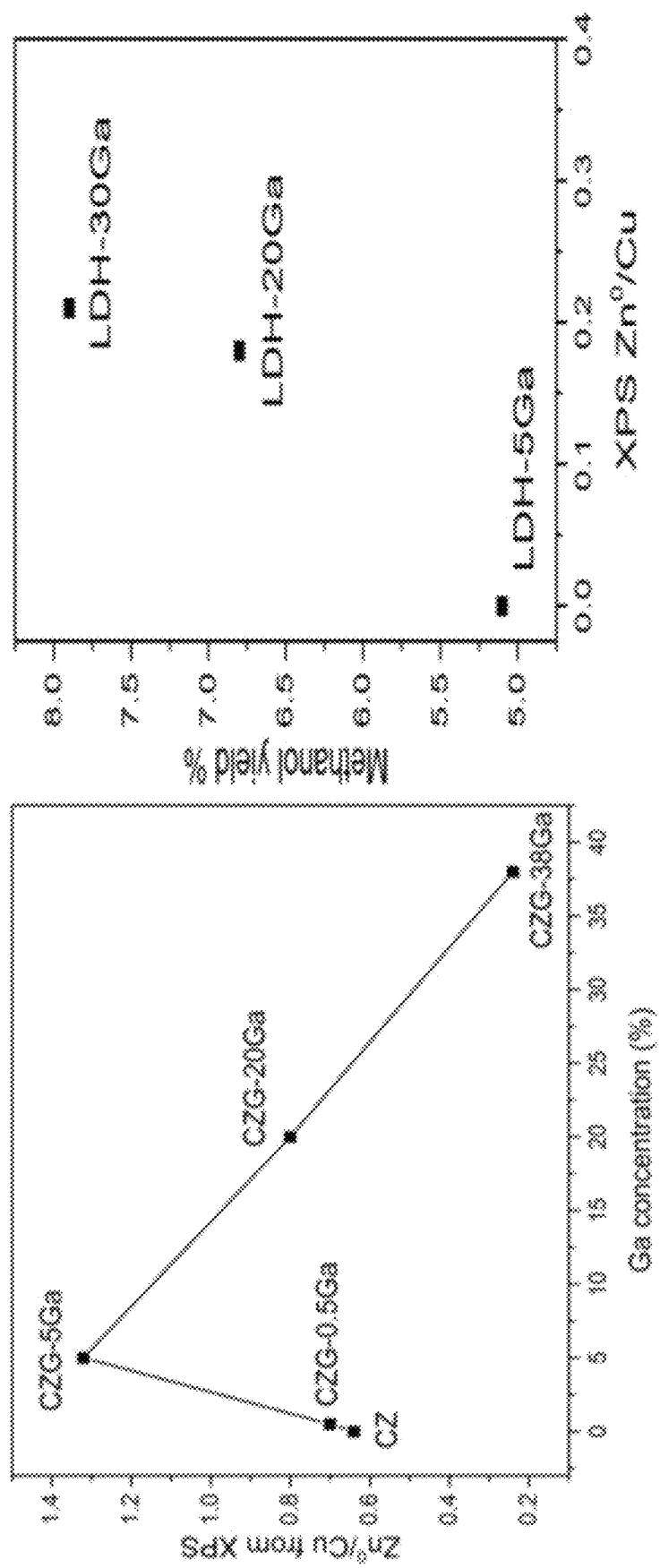
FIG. 12 shows Zn/Cu ratios in CZG samples, as well as Zn/Cu ratio for LDH samples and the impact it has on $CO_2$ hydrogenation.

FIG. 12 shows Zn/Cu ratios in CZG samples, as well as Zn/Cu ratio for LDH samples and the impact it has on CO$_2$ hydrogenation.

Figure 13:
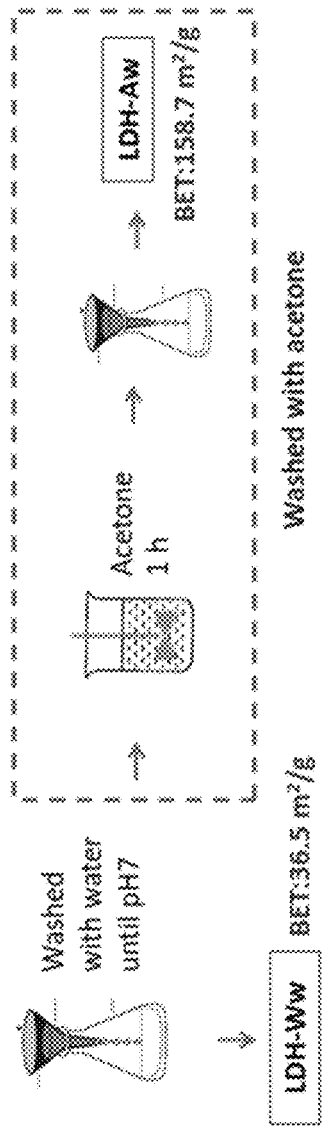
FIG. 13 shows a comparison of conversion, selectivity and yield for LDH30Ga with and without acetone treatment for $CO_2$ hydrogenation to methanol.
Figure 13:
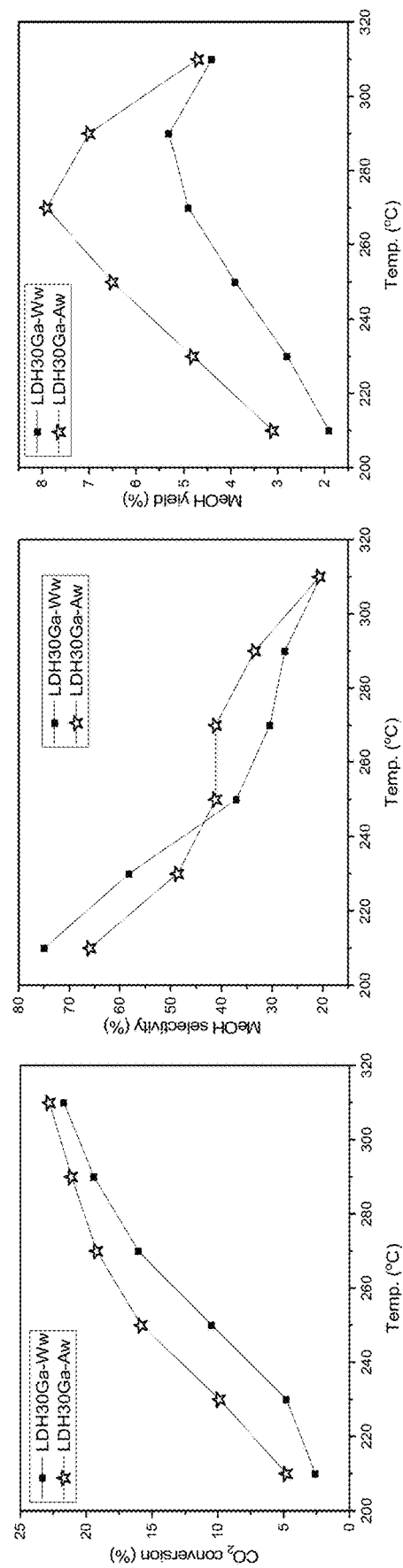

FIG. 13 shows a comparison of conversion, selectivity and yield for LDH30Ga with and without acetone treatment for CO$_2$ hydrogenation to methanol.

Figure 14:
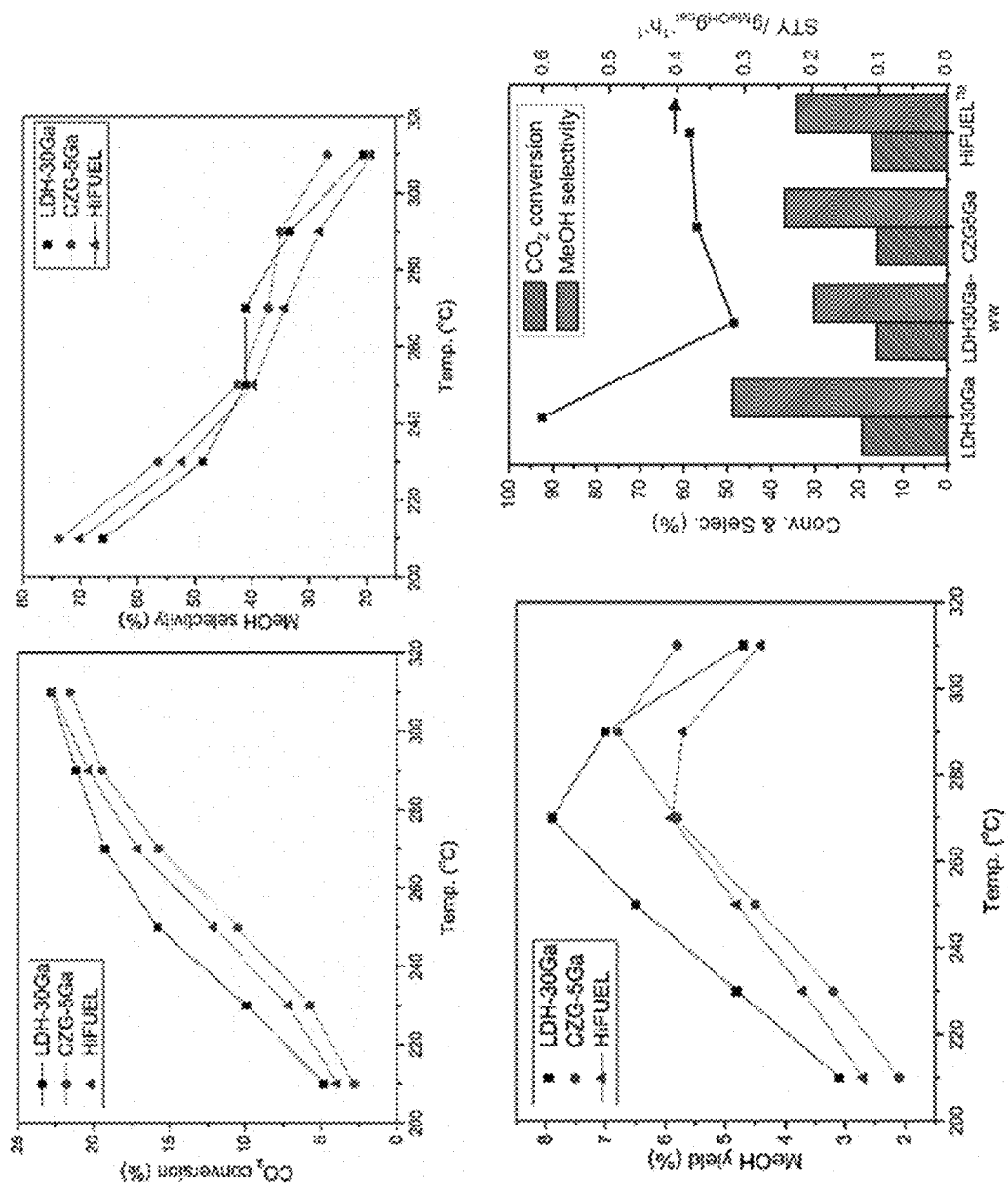
FIG. 14 shows a comparison of conversion, selectivity and yield of CZG5Ga, LDH30Ga, LDH30Ga-ww (water wash) and an industrial sample, HiFUEL with comparable Cu loadings for the $CO_2$ hydrogenation to methanol at 270° C.

FIG. 14 shows a comparison of conversion, selectivity and yield of CZG5Ga, LDH30Ga, LDH30Ga-ww (water wash) and an industrial sample, HiFUEL with comparable Cu loadings for the CO$_2$ hydrogenation to methanol at 270° C.

Figure 15:
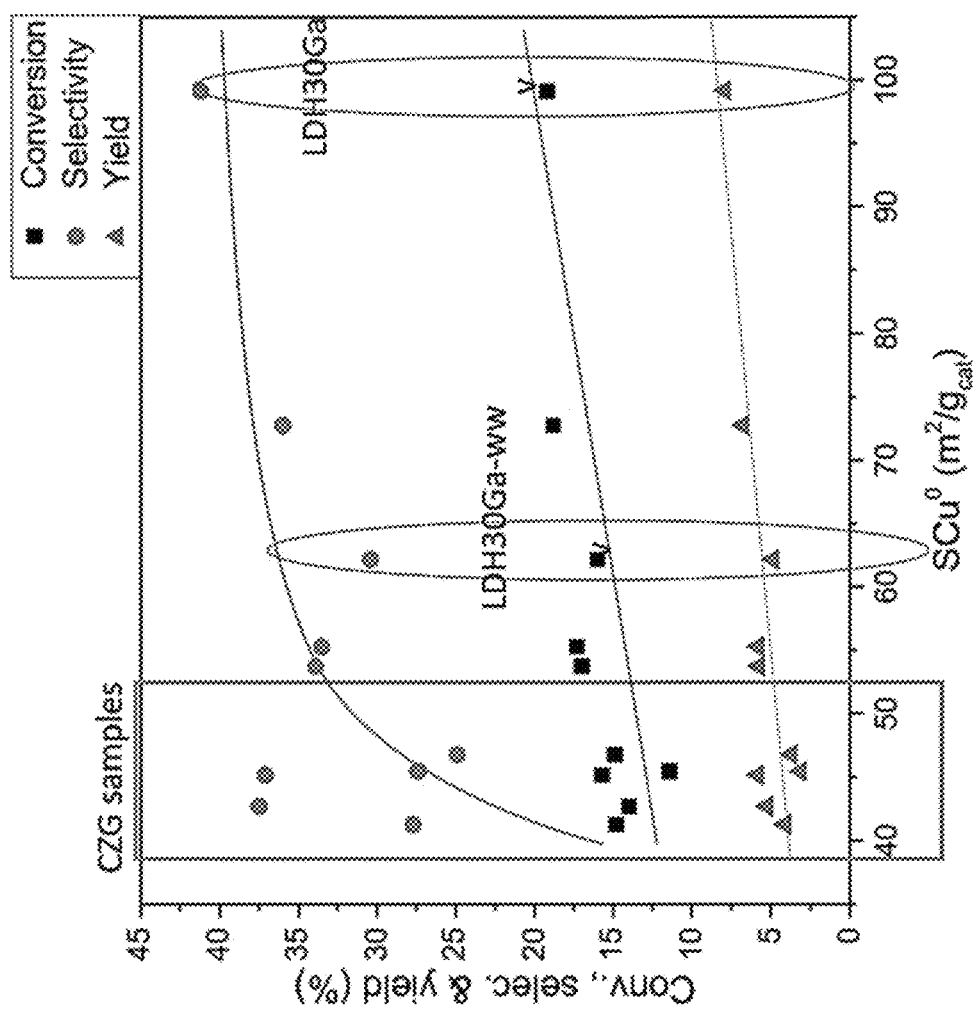
FIG. 15 correlates catalytic performance with Cu surface area for CZG and LDH samples.

FIG. 15 correlates catalytic performance with Cu surface area for CZG and LDH samples.

Example 1—Preparation of Catalysts and Catalytic Intermediates

Using the protocols described below at 1.1 and 1.2, a variety of LDH catalytic precursors (exemplary compounds) and Cu/ZnO or Ga-modified Cu/ZnO catalysts (comparator compounds, termed "CZ" and "CZG") were prepared, as outlined in Table 1 below:

TABLE 1

Synthesis recipes and determined compositions for CZG and LDH samples

| Catalysts | Synthesis recipe Cu:Zn:Ga (mol %) | Cu:Zn:Ga from ICP | |
|---|---|---|---|
| | | Cu:Zn:Ga (wt %) | Cu:Zn:Ga (mol %) |
| CZ | 40:60:0 | 45:55:0 | 44:55:0 |
| CZG-5Ga | 40:55:5 | 43:51:6 | 44:51:5 |
| CZG-10Ga | 40:50:10 | 44:46:10 | 45:45:10 |
| CZG-30Ga | 40:30:30 | 44:26:30 | 45:26:29 |
| CZG-40Ga | 40:20:40 | 42:17:41 | 43:18:39 |
| LDH-10Ga | 40:50:10 | 43:50:7 | 44:49:7 |
| LDH-20Ga | 40:40:20 | 44:41:15 | 45:41:14 |
| LDH-30Ga | 40:30:30 | 45:32:23 | 47:32:21 |
| LDH-40Ga | 40:20:40 | 47:22:31 | 49:22:29 |
| LDH-30Ga-water wash | 40:30:30 | 45:31:24 | 46:31:23 |

Elemental chemical analysis was performed using inductively coupled plasma mass spectrometry (ICP-MS), NexION 300, PerkinElmer.

1.1—Synthesis of AMO-LDH Pre-Catalysts Via Base Solution

A metal precursor solution was added drop-wise into a base solution under rapid stirring. During this nucleation step, the pH value was constantly controlled by adding drop-wise a NaOH solution. Nitrogen aging for 16 hours, the precipitate was washed with DI water until the pH was close to 7. Then, the obtained wet cake solid was dispersed into acetone liquid followed by stirring for 1-2 hours. At the end of this dispersion step, the resultant solid was filtered and washed thoroughly with acetone. The final product was dried overnight in a vacuum oven at room temperature. The LDHs were labelled LDH-xGa, wherein x indicates the mole % of Ga (see Table 1). As described in the literature, the powder sample with and without acetone AMO treatment showed a large difference in their surface area per gram basis[21]. Typically, the LDH-30Ga-water wash (no acetone treatment) and the same powder with acetone treatment (LDH-30Ga) gave 36.5 m$^2$g$^{-1}$ and 158.7 m$^2$g$^{-1}$, respectively. The procedure for the synthesis is graphically summarized in FIG. 1.

1.2—Synthesis of CZG Catalysts by Co-Precipitation (Comparator Catalyst)

Ga$^{3+}$ modified Cu/ZnO catalysts were synthesized using a pH-controlled co-precipitation method[22]. The metal precursors were hydrated metal nitrate salts: Cu(NO$_3$)$_2$·3H$_2$O (Aldrich), Zn(NO$_3$)$_2$·6H$_2$O (Aldrich), and Ga(NO$_3$)$_3$·9H$_2$O (Aldrich). For a typical preparation the metal nitrates [3.77 g Cu(NO$_3$)$_2$·3H$_2$O; 5.53 g Zn(NO$_3$)$_2$·6H$_2$O; 0.75 g Ga(NO$_3$)$_3$·9H$_2$O] were dissolved completely in 100 mL deionized water. A Na$_2$CO$_3$ aqueous solution was prepared by dissolving 3.50 g of Na$_2$CO$_3$ in 100 mL of DI water. The solutions were added simultaneously into a plastic reactor containing 250 mL of preheated DI water. A delivery pump with two 50 mL syringes was used to inject the precursor metal nitrate solution at a constant rate of 0.42 mL/min in an automatic and reproducible manner. An HPLC pump was used to deliver the Na$_2$CO$_3$ solution at a rate of 0.35-0.70 mL/min. The mixture was stirred at 1000 rpm, with pH of the precipitating solution carefully maintained at 6.5. The precipitation process took place at around 80° C. The pH of the liquid was measured using a temperature-dependent pH meter and was controlled at pH 6.5, with an error range of ±0.1. After aging for 16 h, the precipitate was extracted by centrifugation at 5000 rpm. The centrifuged precipitate was washed with DI water five times at 5000 rpm to remove residual Na$^+$ ions. The resulting wet solid was dried in air at 80° C. overnight and then calcined in static air, at a ramp of 5° C./min up to 330° C. for 3 h to produce the final catalyst. The catalysts were labelled as CZ (contains no Ga) and CZG-xGa (x indicates the mole % of Ga)—see Table 1. A typical measured surface area of CZG5Ga was 84.6 m$^2$g$^{-1}$. Two equal portions of the powders were rinsed in acetone for 1 h (CZG5Ga-A1) and 18 h (CZG5Ga-A2) before they were dried. The measured surface areas were 82.0 m$^2$g$^{-1}$ and 93.7 m$^2$g$^{-1}$, respectively. The procedure for the synthesis is graphically summarized in FIG. 2.

Example 2—Powdered X-ray Diffraction (XRD)

The X-ray diffraction (XRD) profile was collected by a Philips PW-1729 diffractometer with Bragg-Brentano focusing geometry using Cu Kα radiation (lambda=1.5418 Å) from a generator operating at 40 kV and 40 mA. Table 2 shows the phase symbol, chemical formula and PDF number which are used in this work.

TABLE 2

Phase symbol, chemical formula and PDF number which are used in this work.

| Phase symbol | Formula | PDF# |
|---|---|---|
| A: aurichalcite | (Cu,Zn)$_5$(CO$_3$)$_2$(OH)$_{16}$ | 82-1253 |
| M: Malachite | (Cu,Zn)$_2$(CO$_3$)(OH)$_2$ | 75-1163 |
| Z: zincite | ZnO | 36-1451 |
| T: tenorite | CuO | 05-0661 |
| S: Spinel structure | ZnGa$_2$O$_4$ | 86-0415 |
|  | CuGa$_2$O$_4$ | 44-0183 |
| #: Aluminum | Al | 85-1327 |

Figure 3A:
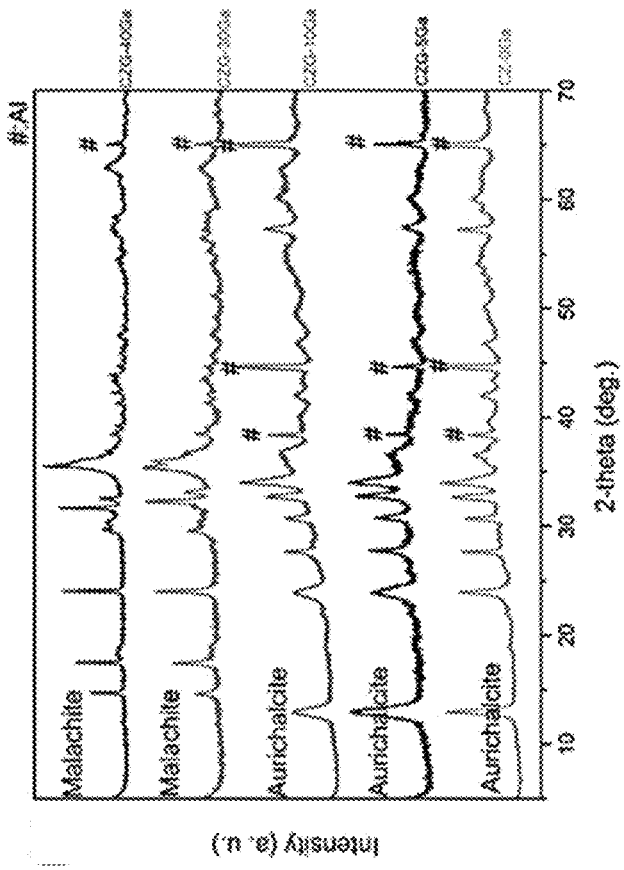
FIG. 3(a) shows XRD profiles of freshly prepared CZG catalyst.

With the introduction of Ga$^{3+}$ into Cu/ZnO catalyst, a series of CZG catalysts were prepared using a simple co-precipitation method with careful control of precursor injection rate, pH value and precipitation temperature to form the CZG hydroxyl-carbonate precursor phases. From the XRD patterns, a dominant, aurichalcite phase of (Cu, Zn)$_5$(CO$_3$)$_2$(OH)$_{16}$ with a high dispersion of Ga species from 0, 5, 20% Ga concentration are seen in FIG. 3a for the freshly prepared samples. At the Ga concentrations of 30 or 40 mole %, zincian malachite phase of (Cu,Zn)$_2$(CO$_3$)(OH)$_2$ are preferably formed. The formation of these two hydroxyl-carbonate phases has been widely reported in literature using related co-precipitation preparation method[22]. The use of high Ga concentration relative to Cu/Zn causing switching of the dominant aurichalcite phase to malachite phase is interesting. Upon 330° C. calcination (FIG. 3b), for the sample without the addition of Ga, phases of CuO and ZnO are clearly identified. As long as Ga is included, a spinel phase of MGa$_2$O$_4$ (M=Zn/Cu) phase formed together with ZnO/CuO over the whole Ga range of 5-40%.

As can be seen in FIG. 3c that samples prepared by AMO-LDH method via base solution give rise to phase pure ((Cu,Zn)$_{1-x}$Ga$_x$)(OH)$_2$(CO$_3$)$_{x/2}$·mH$_2$O·n(C$_3$H$_6$O) {AMO CuZnGa—CO$_3$ LDHs} with increasing crystallinity at or above 20% Ga. The Bragg reflections at 2θ ca. 12°, 24°, and 35° were attributed to (0 0 3), (0 0 6), and (0 0 9) crystal planes in the layered structure with a rhombohedral symmetry (R3)[23]. The rhombohedral symmetry of LDH30Ga was further confirmed by synchrotron XRD analysis (FIG. 4a) revealing the lattice parameters of a, b=3.11 Å, c=22.64 Å. A best fit model indicates monodispersed spheres with average diameter of 9.48 nm which equivalents to an average ~4 layers of the LDH structure (ultrathin LDH). In addition to intense Bragg reflections at 2θ=12°, 24°, and 35°, the broad and asymmetric reflections were also observed at 2θ=36°, 39°, and 47°, ascribed to (0 1 2), (0 1 5), and (0 1 8) crystal planes, respectively for the sample with the highest 40% Ga loading (FIG. 4b). This indicates a homogeneous dispersion of various cations in the hydroxide layers[24]. No other crystalline phases are observed from the LDH samples of 20, 30 and 40% mole Ga. The three Ga concentrations correspond to LDH structure of (Cu$_{45}$Zn$_{41}$Ga$_{14}$)(OH)$_2$(CO$_3$)$_7$, (Cu$_{47}$ZN$_{32}$Ga$_{21}$)(OH)$_2$(CO$_3$)$_{10.5}$ and (Cu$_{49}$Zn$_{22}$Ga$_{29}$)(OH)$_2$(CO$_3$)$_{14.5}$; respectively according to the ICP analyses (Table 1). The 30% mole Ga sample is expected to be more stable than the other two samples. This is because the stability of LDH structure depends critically on electrostatic/steric effect(s) at M$^{2+}$:M$^{3+}$ ratio. For example, M$^{3+}$/M$^{2+}$>0.5 in the latter formulation with finite Ga$^{3+}$ size may create a large distortion in LDH layers. Similarly, the lower M$^{3+}$/M$^{2+}$ ratio in 20% mole Ga is anticipated to be relatively unstable as compared to the conformation of amorphous precipitates (such as hydroxides and hydroxycarbonates)[23]. Below this Ga concentration, amorphous phase is recorded. Similarly, adding 40 mole % Ga in the synthesis ($M^{3+}/M^{2+}>0.5$) leads to stronger electrostatic interaction between the layers due to the presence of higher amount of stoichiometric intercalated carbonate anions. This creates thicker LDH layers (FIGS. 4b-d), which is difficult to disrupt (exfoliate) by the AMO solvent treatment. Interestingly, by using the same calcination temperature to the LDH samples as was prepared to the CZG samples, no formation of spinel structure occurred (FIG. 3d). This clearly indicates that LDHs have a kinetically more stable phase than the hydroxyl-carbonate phases. Although the AMO-LDHs may show lower decomposition temperatures compared to those prepared by conventional synthesis, LDHs normally have two typical distinct thermal events around 200° C. (noted as T1) and 400° C. (noted as T2) evaluated by thermogravimetric analysis (FIG. 4e). The weight loss below T1 is due to desorption of physisorbed and intercalated solvents, which will form a reversible amorphous phase. After T1, the hydroxyl groups start to decompose and gradually transform the LDH structure. This reaches a maximum at above 400° C. (T2), and is ascribed to the partial decomposition of carbonate anions and complete dehydroxylation of the metal hydroxide layers[21]. Thus, the use of 330° C. calcination temperature only gives the single amorphous phase derived from $(Cu_{47}Zn_{32}Ga_{21})(OH)_2(CO_3)_{10.5}$ LDH structure (30% mole Ga in receipe) without reaching the second stage of the layer structure collapse.

Example 3—Transmission Electron Microscopy (TEM) and Atomic Force Microscopy (AFM)

TEM images were taken using a JEOL 2010 Transmission Electron Microscope at 200 kV. The sample particles were deposited on an Agar Scientific Holey carbon supported copper 400 mesh grid. TEM samples were prepared by sonicating a suitable amount of material in 1 mL ethanol for 15 minutes before drop wise adding the solution onto the copper grid.

Atomic Force Microscopy (AFM) measurements were collected by Agilent 5400 microscope. AFM samples were prepared by deposition of fresh diluted emulsion of LDH samples onto a clean Si wafer by dip coating. The images were obtained with a Si tip cantilever (MikroMasch NSC35/ALBS) working with frequency and force constant of 150 kHz and 4.52 N·m$^{-1}$, respectively, using non-contact mode in air at room temperature. Images were recorded with 512×512 pixels and 0.5-1 Hz scan rate. Processing and analysis of the images were carried out using the PicoView version 1.20.2 software.

In order to determine the textural properties of these samples, TEM and AFM were employed. FIGS. 5a and b show the typical images of the freshly-prepared hydroxy-carbonate phase of CZG5Ga and CZG40Ga prepared by co-precipitation method. It appears that the extended fibrous/sheet like structure is fragmentized in the presence of higher Ga concentration, giving many smaller sizes of mixed phases. On the other hand, the LDH5Ga is similar in textual appearance as CZG5Ga although small sheet-like features are occasionally observed (FIG. 5c). It is noted that the XRD of the AMO-LDH samples with low Ga concentration (LDH5Ga and LDH10Ga) in FIG. 3c show no indication of LDH phase formation. Their $M^{2+}:M^{3+}$ is outside the stability range for LDHs, but probably some mixed phases of hydroxyl-carbonate structures of below the detection limit by the XRD are made, hence giving mixed shapes (particles/fibrous/sheets) in appearance. It is interesting to see the homogeneous sheet-like structure when 30% Ga was used (LDH30Ga), which agrees with the expected layered LDH structure identified by the XRD (FIG. 3c). In addition, single and extremely thin layers of LDH sheets (SXRD shows an average of 4 LDH layers, see FIG. 4a) are indeed evidenced: the morphology matches with their anticipated high surface area (FIG. 2) when acetone was used.

FIG. 6a shows the TEM images of the CZG5Ga after calcination in air atmosphere, suggesting that the formation of mixed metal oxides (appeared as sphere-like particles) can be observed. FIG. 6b-c shows the images of the reduced CZG5Ga sample prepared with $H_2$ treatment at 290° C. (2 h), which gave 5-10 nm Cu rich (shown by EDX) particles with occasionally much larger particles observed. In contrast, the image of calcined LDH30Ga (FIG. 7a) reveals multiple curved sheets assembled mostly of single discrete layers with some edge regions of 2-3 staggered layers, indicating the AMO-LDH precursor can maintain its ultra-thin layered morphology in spite of exhibiting an amorphous phase (FIG. 3d) after calcination. Under identical hydrogen treatment shown in FIGS. 7b-c, many small and rather homogeneous size Cu-rich particles of less than 5 nm (mean size=4.0±0.1 nm) are formed on this positive charged sheet-like structure. In line with the morphology observation of the reduced catalysts, the reduction behavior of the AMO-LDH samples, see FIG. 8, displays more uniform peak profiles compared to the CZG samples. The controlled reduction with the formation of smaller Cu seeds in the AMO-LDH sample clearly reflects that Cu species must be engaged in a stable LDH structure, which offers the fine controlled nucleation and restricted mobility of metal atoms by the high surface, discrete inorganic sheets, thus can lead to small, stable, and homogeneous Cu particles.

The striking reduction in the number of cationic layers via acetone (AMO-solvent) inter-layer disruption produced by the AMO-LDH method (fine particle portion) can be identified by AFM on the 30% Ga ($M^{2+}/M^{3+}$=2.33) sample (FIG. 5e). As can be seen from FIG. 5f that the typical height profile of LDH30Ga sample clearly shows a thickness between 0.8-2.3 nm for selected regions, which corresponds to 1-3 layer LDH platelet according to a 3-layer LDH30Ga structural model intercalated with carbonate anions as depicted in FIG. 5g (for the single cationic layer, the structure stabilized by adsorbed carbonate anions is anticipated). The formation of such ultra-thin nanosheets which separated by discrete cationic layers and balanced by intercalated carbonate anions suggests that acetone dispersion can override the weaker interlayer electrostatic interaction, thus accounting for the dramatic increase in surface area of this sample.

Example 4—Temperature Programmed Reduction (TPR)

TPR measurements were obtained using a ThermoQuest TPRO 110 instrument. Inside the TPR quartz tube, 0.026 g of the calcined catalyst sample was sandwiched between two layers of glass wool with a thermocouple placed in contact with the sample. The TPR tube was then inserted into the instrument for a helium pretreatment. The helium gas pretreatment (He running through the TPR tube at 10 mL min$^{-1}$ at a temperature ramp of 10° C. min$^{-1}$ from 40 to 150° C., then held for 5 min before cooling) cleaned the catalyst surface by removing any absorbed ambient gas molecules. After the pretreatment, a reduction treatment (5% $H_2$ in Argon flowing through the TPR tube at 20 mL min$^{-1}$ at a temperature ramp of 10° C. min$^{-1}$ from 40 to 400° C., then held at 400° C. for 30 min before cooling to room temperature) was carried out to reduce the $Cu^{2+}$ within the sample. Cu(II)O was reduced to $Cu^0$ by the flow of hydrogen gas in the reduction treatment. The consumption of hydrogen gas changed the conductivity of the gas stream; hence, the change in conductivity was measured and calibrated as a function of both temperature and time to produce the TPR profile.

Figure 8B:
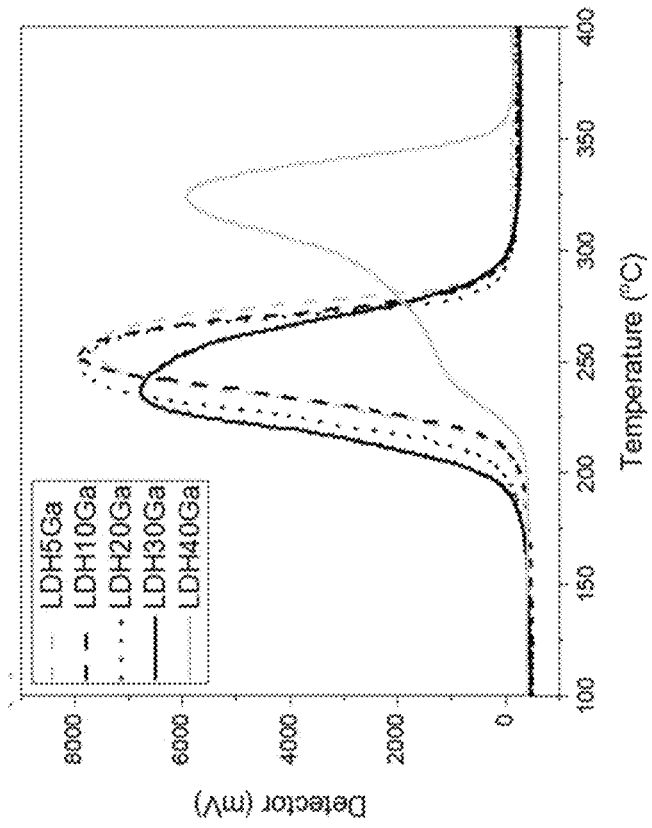
FIG. 8(b) shows temperature programmed reduction (TPR) profile of LDH samples.
Figure 8A:
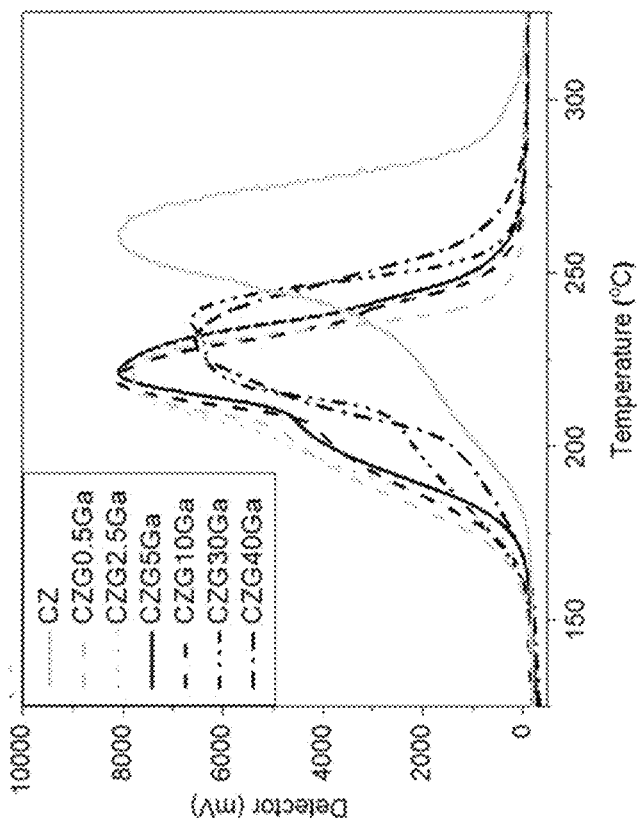
FIG. 8(a) shows temperature programmed reduction (TPR) profile of CZG samples.

The reduction behaviour of calcined CZG and LDH samples was investigated by $H_2$-TPR, and the corresponding reduction profiles are given in FIG. 8. FIG. 8 shows that all samples give virtually the same integral reduction peak area of 5.0±0.5 mmole $H_2$/g-cat corresponding to the complete reduction of $Cu^{2+}$ to $Cu^0$. It is however, interesting to note from FIG. 8a that CZG samples display a complex reduction peak accompanied by shoulders in the temperature range of 150-270° C. This indicates that some reduced Cu species exist in heterogeneous chemical environments (variation in size and structure) hence giving different peak maxima at different reduction temperatures. The reduction range of 150-200° C. (low temperature shoulder) matches with $Cu_2O$ but its content diminishes at higher Ga loading[22]. The higher temperature main peak is attributed to the reduction of CuO. Such a large variation in reduction behaviour of $Cu^+$ and $Cu^{2+}$ would be expected to give large Cu particle size variation as clearly evidenced in the corresponding TEM images (FIG. 6b-c). Without Ga (no spinel), a higher temperature is required for $Cu^{2+}$ reduction.

On the other hand, the reduction profile of more homogeneous LDH samples shown in FIG. 8b gives more uniform peak profile but at higher temperature range of 200-290° C. than that of CZG samples, with no low temperature shoulder peak (absence of $Cu_2O$). This observation also matches the TEM investigation (FIG. 7b-c) that smaller and homogeneous Cu particles can be formed from the reduction of more stable LDH phase. The controlled reduction at higher temperature with smaller seeds clearly reflects that the majority of $Cu^{2+}$ must be engaged in a more stable LDH structure.

Example 5—Cu Surface Area and Dispersion

The dispersion ($D_{Cu}$) and exposed surface area ($S_{Cu}$) of Cu were determined by dissociative $N_2O$ chemisorption followed by hydrogen pulse reduction. $N_2O$ chemisorption was carried out on a Micromeritics AutoChem II 2920 instrument. Before the measurement, 100 mg of calcined sample was reduced at 350° C. in a 5% $H_2$/Ar mixture (50 mL·min$^{-1}$) for 4 h. After cooling to 60° C., the sample was exposed to $N_2O$ (20 mL·min$^{-1}$) for 1 h to ensure complete oxidation of surface metallic copper to $Cu_2O$. Finally, calibrated hydrogen pulse reduction at 300° C. was conducted to determine the amount of surface $Cu_2O$ species. $D_{Cu}$ and $S_{Cu}$ were then calculated by dividing the amount of surface copper by the actual Cu loading determined by ICP-MS.

As previously discussed, Cu surface is generally believed to provide active sites for $CO_2$ hydrogenation[7,8]. As a result, it is important to determine the Cu surface area and dispersion for each of the CZG and LDH catalysts. The Cu loading (determined by ICP), Cu dispersion and Cu surface area/g-cat (determined by $N_2O$ chemisorption[22,23]) for all Cu containing CZG and LDH catalysts were determined accordingly and are shown in Table 3. It is clear from the compiled Cu surface areas and Cu dispersions that CZG samples give consistently lower values than LDH samples, which agrees with a similar behavior observed for the BET surface area analysis that CZG precursors have much lower specific surface areas than the LDH precursors. This again indicates the controlled reduction of $Cu^{2+}$ from high intrinsic surface area. It also shows that the stable LDH structure prerpared by the AMO technique[21] can lead to smaller Cu particles. The best Cu dispersion is seen to be 30 mol % Ga in receipe concentration, which gave the smallest Cu particles having the highest Cu surface area (see Table 3).

TABLE 3

Comparison of Cu loading (determined by ICP), Cu dispersion and Cu surface area/g-cat determined by $N_2O$ chemisorption) for all Cu containing CZG and LDH catalysts.

| Catalysts | Cu loading$^a$ (wt %) | Cu dispersion$^b$ | $S_{Cu}{}^b$ (m$^2$/g$_{cat}$) |
|---|---|---|---|
| CZ | 33.4 | 21.8 | 46.8 |
| CZG5Ga | 31.9 | 22.0 | 45.2 |
| CZG10Ga | 33.9 | 19.5 | 42.7 |
| CZG30Ga | 32.7 | 19.6 | 41.3 |
| CZG40Ga | 33.5 | 21.1 | 45.5 |
| LDH10Ga | 34.3 | 24.4 | 53.8 |
| LDH20Ga | 33.4 | 33.8 | 72.8 |
| LDH30Ga | 33.5 | 46.0 | 99.2 |
| LDH40Ga | 37.9 | 22.6 | 55.3 |
| LDH30Ga-ww (water wash) | 34.3 | 28.1 | 62.2 |

$^a$Determined by ICP;
$^b$Dispersion and specific surface area of metallic Cu determined by $N_2O$ chemisorption.

Example 6—X-ray Photoelectron Spectroscopy (XPS)

After reduction at 290° C., samples were carefully transferred in a glove bag filled with nitrogen to prevent the air exposure and analyzed by XPS. The XPS was performed using a Quantum 2000 Scanning ESCA Microprob instrument (Physical Electronics) equipped with an Al Kα X-ray radiation source (hv=1486.6 eV). A flood gun with variable electron voltage (from 6 eV to 8 eV) was used for charge compensation. The raw data were corrected for substrate charging with the BE of the C peak (284.5 eV), as shown in the XPS handbook. The measured spectra were fitted using a least-squares procedure to a product of Gaussian-Lorentzian functions after removing the background noise. The concentration of each element was calculated from the area of the corresponding peak and calibrated with the sensitivity factor of Wagner.

Figure 9C:
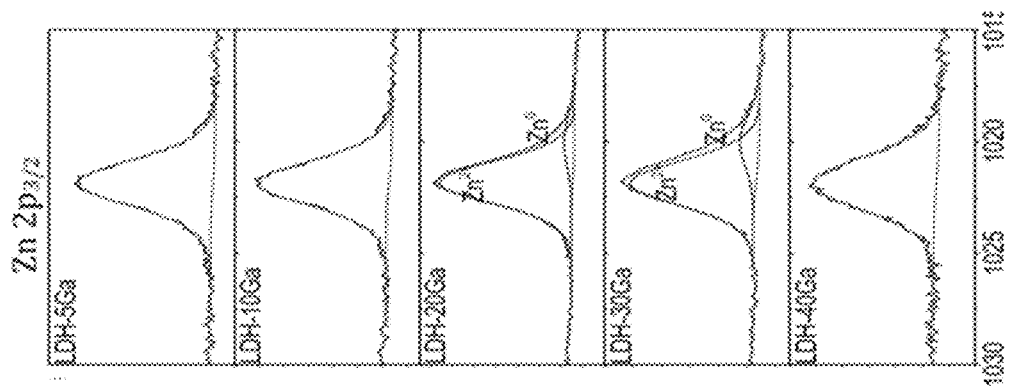
FIG. 9(c) shows XPS spectra of reduced LDH samples of Zn 2 $p_{3/2}$ peaks at various Ga concentrations.
Figure 9B:
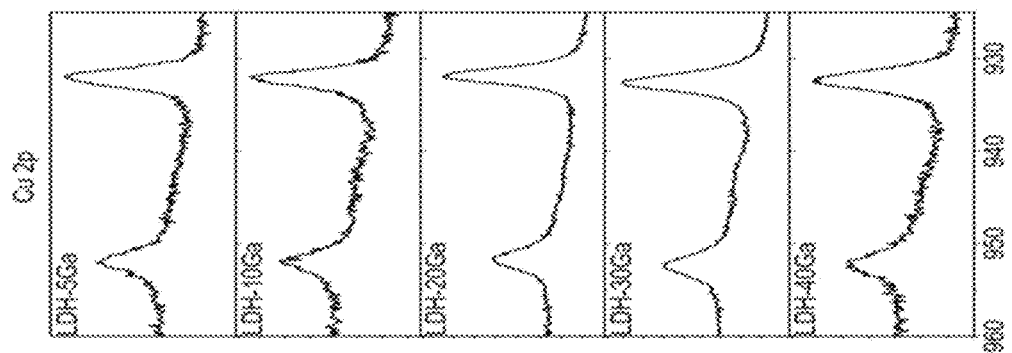
FIG. 9(b) shows XPS spectra of reduced LDH samples of Cu 2p peaks.
Figure 9A:
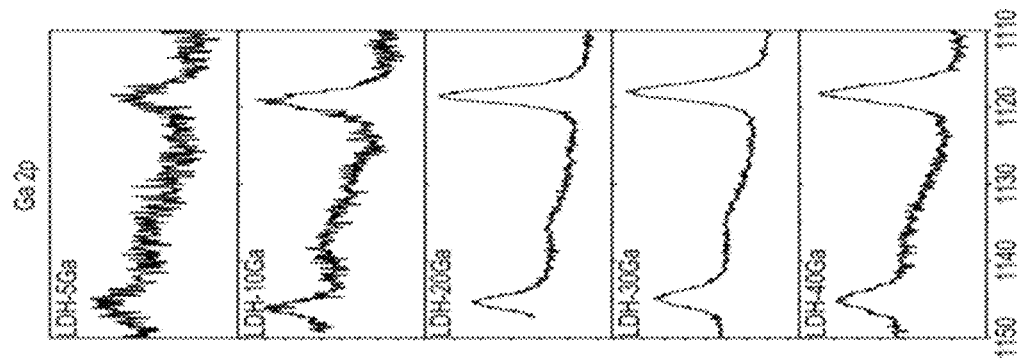
FIG. 9(a) shows XPS spectra of reduced LDH samples of Ga 2p peaks.

The XPS results of the LDH samples with various Ga contents are revealed in FIG. 9. FIG. 9a clearly shows that the progressive increase in Ga peak size at increasing Ga content. In comparison with the peak position with reference to adventurous carbon, Ga is still maintained as $Ga^{3+}$ with no sign of reduction[25]. However, the positions of $2p_{1/2}$ and $2p_{3/2}$ of Cu (FIG. 9b) match well with those of $Cu^0$ and their peak sizes remain the same at increasing Ga concentrations. This again suggests that $Cu^{2+}$ is totally reduced from the LDH samples upon the pre-reduction treatment in $H_2$ at 290° C. The peak position of Zn $2p_{3/2}$ shown in FIG. 9c of LDH samples matches with $Zn^{2+}$ showing that it stays unreduced in the solid structure[25]. However, there is a small degree of $Zn^{2+}$ reduction to $Zn^0$ at the Ga concentrations of 20 and 30 mole % which correspond to the maximum amounts of LDH phases with high surface areas. Through careful deconvolution, the broader peak can be into two sub-peaks of $Zn^{2+}$ (1023 eV) and $Zn^0$ (1021 eV). Comparatively, LDH5Ga, LDH10Ga and LDH40Ga shows no $Zn^0$ signal which is probably due to their low surface area that cannot facilitate the reduction of ZnO.

Example 7—CO$_2$ Hydrogenation

Catalytic tests in hydrogenation of CO$_2$ to produce methanol were carried out in a tubular fixed bed reactor (12.7 mm outside diameter) by using a catalyst weight of 0.1 g. CO$_2$/H$_2$ reaction mixture with molar ratio of 1:3 was fed at a rate of 30 stp mL min$^{-1}$ (stp=standard temperature and pressure; P=101.3 kPa, T=298 K) through the catalyst bed. Before each test, the catalyst was pre-reduced at 290° C. for 2 h under the H$_2$ flow (20 stp mL min$^{-1}$). The products were analysed by a gas chromatograph equipped with calibrated thermal conductivity detector (TCD) and flame ionization detector (FID).

The catalytic performances of Cu containing CZG and LDH samples were evaluated and are presented in FIG. 10 and FIG. 11, respectively. The major product for all catalysts is methanol and the main by-product is CO under operating conditions of H$_2$:CO$_2$ (molar)=3:1, T=190-310° C., P=4.5 MPa and WHSV=18,000 mL·g$_{cat}^{-1}$·h$^{-1}$. The activity measurements were taken after at least 2 h on the stream at each selected temperature. FIG. 10 shows similar performances of CZ and CZG samples due to their similar Cu surface areas and dispersions (Table 3). In general, CZG5Ga shows a slightly better performance than all the other CZG samples. The methanol yield reaches the optimal value at 280-290° C. and drops with further increasing temperature which suggests the approach of the thermodynamic limit. Interestingly, according to FIG. 11, the LDH samples which show higher Cu surface areas and dispersions, particularly the LDH20Ga and LDH30Ga (see Table 3) also give higher methanol selectivities and yields than CZG5Ga at 270° C. LDH30Ga gave the best catalytic performance, achieving an 8% methanol yield. This supports the literature's suggestion that the Cu surface provides active sites for this hydrogenation reaction[7]. It is thus advantageous to make larger surface Cu with higher metal dispersion (smaller Cu particle size) from a stable solid precursor upon reduction. In this respect, LDH Cu containing samples appear to be more superior to those prepared by conventional co-precipitation. FIG. 9 also indicates that there is a small degree of deep reduction of Zn$^{2+}$ to Zn$^0$ over these samples. As a result, it becomes more significant for those samples (CZG5Ga, LDH20Ga and LDH30Ga) with higher Cu dispersions. The higher Zn/Cu ratios revealed in FIG. 12 show a good correlation with methanol yields with both CZG and LDH samples which suggest the importance of Zn decoration on Cu cluster for optimal methanol synthesis.

FIG. 13 shows a comparison of the Cu containing LDH30Ga with and without the acetone treatment. Clearly, the higher surface area and thinner LDH precursor LDH30Ga-Aw with acetone treatment (158.7 m$^2$g$^{-1}$) gave higher conversion and yield than that of LDH30Ga-Ww (36.5 m$^2$g$^{-1}$) towards methanol in the hydrogenation of CO$_2$. Thus, the exposure of ultrathin LDH can allow controlled reductions of Cu and Zn from the layer structure to give higher Cu dispersion decorated with Zn atoms which form active sites for this catalyzed reaction.

The catalytic performances of CZG5Ga and the commercial HiFUEL catalyst has been compared with LDH30Ga with and without acetone treatment having comparable Cu loadings (FIG. 14). LDH30Ga (acetone washing) exhibits better performances amongst the four samples. when the final wet slurry of LDH was dispersed with an AMO solvent (acetone), it dramatically enhances the surface area of the final material (S$_{LDH30Ga}$=158.71±0.17 m$^2$g$^{-1}$ vs S$_{LDH30Ga-Ww}$=36.51±0.10 m$^2$g$^{-1}$, FIG. 1) by exfoliating the cationic multilayers (intercalated with carbonate anions) approaching to 1-3 layers. This discrete cationic layer can facilitate the formation of small (~4 nm) and homogeneous Cu particles decorated with trace Zn atoms with narrow size distribution, which lead to higher CO$_2$ conversion and methanol production. In comparison with other reported Cu containing LDH samples, the simple and non-optimized AMO-LDH (LDH30Ga) sample shows increased weight time yield of methanol, and can sustain a higher GHSV (Table 4).

TABLE 4

Comparison of methanol space time yields of selected catalysts with the catalysts of the invention

| Catalyst | P (bar), T (° C.) | Space velocity | H$_2$/CO$_2$ | Catalytic Performance STY[b] | Ref. |
|---|---|---|---|---|---|
| LDH30Ga | 45, 270 | (W) 18000 mL g$^{-1}$ h$^{-1}$ | 3 | 0.6 | This work |
| LDH30Ga-ww | 45, 270 | (W) 18000 mL g$^{-1}$ h$^{-1}$ | 3 | 0.3 | |
| CZG5Ga | 45, 270 | (W) 18000 mL g$^{-1}$ h$^{-1}$ | 3 | 0.4 | |
| JM-HiFUEL ™ | 45, 270 | (W) 18000 mL g$^{-1}$ h$^{-1}$ | 3 | 0.4 | |
| LDH (Cu, Zn, Al, Y) | 50, 250 | (W) 10000 mL g$^{-1}$ h$^{-1}$ | 3 | 0.4 | 23 |
| Cu on LDH (Zn, Al, Zr) supports | 50, 250 | (W) 7500 mL g$^{-1}$ h$^{-1}$ | 3 | 0.3 | 26 |
| LDH (Cu, Zn, Al, Y) | 50, 250 | (W) 12000 mL g$^{-1}$ h$^{-1}$ | 3 | 0.5 | 27 |
| LDH (Cu, Zn, Al, Ga) | 60, 250 | (W) 10000 mL g$^{-1}$ h$^{-1}$ | Syngas H$_2$:CO:CO$_2$:He = 72:10:4:14 | ~0.4 | 28 |
| In$_2$O$_3$/ZrO$_2$ | 50, 300 | (G) 16,000 h$^{-1}$ | 4 | 0.3 | 29 |
| Pd@Zn | 45, 270 | (W) 18000 mL g$^{-1}$ h$^{-1}$ | 3 | ~0.6 | 30 |

[a](G) = GHSV = volume flow rate/bed volume, (W) = WHSV = mass flow rate/catalyst mass.
[b]Space time yield of methanol (g$_{MeOH}$ · g$_{cat}^{-1}$ · h$^{-1}$)

FIG. 15 provides a correlation of the catalytic performance with Cu surface area for CZG and LDH samples.

While specific embodiments of the invention have been described herein for the purpose of reference and illustration, various modifications will be apparent to a person skilled in the art without departing from the scope of the invention as defined by the appended claims.

REFERENCES

1. Yu, K. M. Curcic, I. Gabriel, J. & Tsang, S. C. E. *ChemSusChem.* 1, 893-899 (2008).
2. Turner, J. et al. Int. *J. Energy Res.* 32, 379-407 (2008).
3. Song, C. *Catal. Today.* 115, 2-32 (2006).
4. Fujitani, T. Nakamura, *J. Appl. Catal. A.* 191, 111-129 (2000).
5. Liao, F. Zeng, Z. Eley, C. Lu, Q. Hong, X. & Tsang, S. C. E. *Angew. Chem. Int. Ed.* 51, 5832-5836 (2012).
6. Zander, S. et al. *Angew. Chem. Int. Ed.* 52, 6536-6540 (2013).
7. Spencer, M. S. *Top. Catal.* 8, 259-266 (1999).
8. Fujitani, T. & Nakamura, *J. Catal. Lett.* 56, 119-124 (1998).
9. Kanai, Y. et al. *Catal. Lett.* 27, 67-78 (1994).
10. Fujita, S. Usui, M. Ito, H. Takezawa, N. *J. Catal.* 157, 403-413 (1995).
11. Choi, Y. Futagami, K. Fujitani, T. Nakamura, *J. Appl. Catal. A.* 208, 163-167 (2001).
12. Behrens, M. et al. *Science.* 336, 593-897 (2012).
13. Arena, F. Barbera, K. Italiano, G. Bonura, G. & Spadaro, L. *J. Catal.* 249, 185-194 (2007).
14. Saito, M. Fujitani, T. Takeuchi, M. & Watanabe, T. *Appl. Catal. A.* 138, 311-318 (1996).
15. Kurtz, M. Wilmer, H. Genger, T. Hinrichsen, O. & Muhler, M. *Catal. Lett.* 86, 77-80 (2003).
16. An, X. et al. *Catal. Lett.* 118, 264-269 (2007).
17. Weigel, J. Koeppel, R. A. Baiker, A. & Wokaun, A. *Langmuir.* 12, 5319-5329 (1996).
18. Yu, K. M. et al. *Nat. Commun.* 3, 1230 (2012).
19. Tong, W. Cheung, K. West, A. Yu, K. M. & Tsang, S. C. E. *Phys. Chem. Chem. Phys.* 15, 7240-7248 (2013).
20. Tong, W. West, A. Cheung, K. Yu, K. M. & Tsang, S. C. E. *ACS catal.* 3, 1231-1244 (2013
21. Chen, C. Yang, M. Wang, Q. Buffet, J. C. & O'Hare, D. *J. Mater. Chem. A.* 2, 15102-15110 (2014).
22. Li, M. M-J. Zheng, J. Qu, J. Liao, F. Raine, E. Kuo, W. C. H. Su, S. S. Po, P. Yuan Y. & Tsang, S. C. E. *Sci. Rep.* 6, 20527 (2016).
23. Gao, P. Zhong, L. Zhang, L. Wang, H. Zhao, N. Wei, W. & Sun, Y. *Catal. Sci. Technol.* 5, 4365-4377 (2015).
24. Cheng, J. Wang, X. P. Yu, J. J. Hao, Z. P. & Xu, Z. P. *J. Phys. Chem. C.* 115, 6651-6660 (2011).
25. Data from Thermal Scientific XPS (http://xpssimplified.com/index.php).
26. Gao, P. Feng, L. Xiao, F. Zhao, N. Wei, W. Zhong, L. & Sun, Y. *Catal. Today.* 194, 9-15 (2012).
27. Gao, P.; Li, F.; Zhao, N.; Xiao, F.; Wei, W.; Zhong, L.; Sun, Y. Influence of Modifier (Mn, La, Ce, Zr and Y) on the Performance of Cu/Zn/Al Catalysts via Hydrotalcite-like Precursors for $CO_2$ Hydrogenation to Methanol. *Appl. Catal. A Gen.*, 468, 442-452 (2013).
28. Kühl, S. Schumann, J. Kasatkina, I. Hävecker, M. Schlögl, R. & Behrens, M. *Catal. Today.* 246, 92-100 (2015).
29. Martin, O.; Martin, A. J.; Mondelli, C.; Mitchell, S.; Segawa, T. F.; Hauert, R.; Drouilly, C.; Curulla-Ferré, D.; Pérez-Ramirez, J. Indium Oxide as a Superior Catalyst for Methanol Synthesis by $CO_2$ Hydrogenation. *Angew. Chemie-Int. Ed.*, 55, 6261-6265 (2016).
30. Liao, F.; Wu, X.-P.; Zheng, J.; Li, M. M.-J.; Kroner, A.; Zeng, Z.; Hong, X.; Yuan, Y.; Gong, X.-Q.; Tsang, S. C. E. A Promising Low Pressure Methanol Synthesis Route from $CO_2$ Hydrogenation over Pd@Zn Core-shell Catalysts. *Green Chem.*, 19, 270-280 (2017).

The invention claimed is:

1. A layered double hydroxide of formula (I) shown below

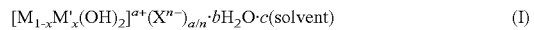

$$[M_{1-x}M'_x(OH)_2]^{a+}(X^{n-})_{a/n} \cdot bH_2O \cdot c(\text{solvent}) \quad (I)$$

wherein
M represents a mixture of divalent cations comprising $Cu^{2+}$ and $Zn^{2+}$;
M' represents $Ga^{3+}$, and optionally one or more other trivalent cations selected from $Al^{3+}$ and $Y^{3+}$;
$0 < x \leq 0.4$;
$0 < b \leq 10$;
$0 < c \leq 10$;
X represents at least one anion;
n is the charge on anion X and has a value of 1 or 2;
$0.2 \leq a \leq 0.4$; and
the solvent represents at least one organic solvent capable of hydrogen-bonding to water;
wherein a molar ratio of Cu:Zn:Ga within the layered double hydroxide of formula (I) is 1:(0.42-1.00):(0.18-0.65); and
wherein, when the layered double hydroxide is thermally treated at a temperature of 250-400° C. the thermally treated layered double hydroxide is amorphous, optionally containing traces of ZnO phase, and no spinel phase is formed.

2. The layered double hydroxide of claim 1, wherein M' is $Ga^{3+}$.

3. The layered double hydroxide of claim 2, wherein M represents a mixture of divalent cations comprising $Cu^{2+}$ and $Zn^{2+}$, as well as one or more other divalent cations selected from $Mg^{2+}$, $Fe^{2+}$, $Ca^{2+}$, $Sn^{2+}$, $Ni^{2+}$, $Co^{2+}$, $Mn^{2+}$ and $Cd^{2+}$.

4. The layered double hydroxide of claim 2, wherein M represents a mixture of divalent cations consisting of $Cu^{2+}$ and $Zn^{2+}$.

5. The layered double hydroxide of claim 4, wherein X is carbonate.

6. The layered double hydroxide of claim 5, wherein the solvent is at least one of acetone, acetonitrile and ethanol.

7. The layered double hydroxide of claim 1, wherein X represents at least one anion selected from a halide, an inorganic oxyanion, and an organic anion.

8. The layered double hydroxide of claim 1, wherein the solvent is at least one of acetone, acetonitrile, dimethylformamide, dimethyl sulphoxide, dioxane, ethanol, methanol, n-propanol, isopropanol, tetrahydrofuran, ethyl acetate, n-butanol, sec-butanol, n-pentanol, n-hexanol, cyclohexanol, diethyl ether, diisopropyl ether, di-n-butyl ether, methyl tert-butyl ether (MTBE), tert-amyl methyl ether, cyclopentyl methyl ether, cyclohexanone, methyl ethyl ketone (MEK), methyl isobutyl ketone (MIBK), methyl isoamyl ketone, methyl n-amyl ketone, furfural, methyl formate, methyl acetate, isopropyl acetate, n-propyl acetate, isobutyl acetate, n-butyl acetate, n-amyl acetate, n-hexyl acetate, methyl amyl acetate, methoxypropyl acetate, 2-ethoxyethyl acetate and nitromethane.

9. The layered double hydroxide of claim 1, wherein M is $Cu^{2+}$ and $Zn^{2+}$ and M' is $Ga^{3+}$, and wherein a molar ratio of Cu:Zn:Ga is 1:(0.62-0.72):(0.40-0.50).

10. A thermally-treated layered double hydroxide, comprising a thermally-treated form of the layered double hydroxide of claim 1.

11. The thermally-treated layered double hydroxide of claim 10, wherein the thermally-treated layered double hydroxide comprises a calcined form of the layered double hydroxide of claim 1.

12. A process for preparation of methanol by hydrogenation of carbon dioxide and/or carbon monoxide, the process comprising the step of:
   a. providing the thermally-treated layered double hydroxide as claimed in any of claims 10 and 11;
   b. reducing the thermally-treated layered double hydroxide provided in step a) to yield a catalyst; and
   c. contacting the catalyst obtained in step b) with a mixture of hydrogen and one or both of carbon monoxide and carbon dioxide.

13. The process of claim 12, wherein step c) comprises contacting the catalyst with a mixture of carbon dioxide and hydrogen.

14. The process of claim 12, wherein step c) is conducted at a temperature of 200-350° C.

15. The catalyst of claim 12, wherein the process has a Cu dispersion of >20%, or wherein the catalyst has a Cu loading of 30-40% by weight relative to a total weight of the catalyst.

* * * * *